US012590165B2

(12) United States Patent
Sethi et al.

(10) Patent No.: US 12,590,165 B2
(45) Date of Patent: Mar. 31, 2026

(54) METHODS AND MATERIALS FOR IDENTIFYING AND TREATING MEMBRANOUS NEPHROPATHY BASED ON ELEVATED SEMAPHORIN 3B

(71) Applicant: Mayo Foundation for Medical Education and Research, Rochester, MN (US)

(72) Inventors: Sanjeev Sethi, Rochester, MN (US); Fernando C. Fervenza, Rochester, MN (US); Benjamin J. Madden, Stewartville, MN (US); M. Cristine Charlesworth, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 802 days.

(21) Appl. No.: 17/758,361

(22) PCT Filed: Mar. 5, 2021

(86) PCT No.: PCT/US2021/021170
§ 371 (c)(1),
(2) Date: Jul. 5, 2022

(87) PCT Pub. No.: WO2021/178863
PCT Pub. Date: Sep. 10, 2021

(65) Prior Publication Data
US 2023/0348610 A1      Nov. 2, 2023

Related U.S. Application Data

(60) Provisional application No. 62/986,224, filed on Mar. 6, 2020.

(51) Int. Cl.
| | | |
|---|---|---|
| *A61P 13/12* | (2006.01) | |
| *C07K 16/28* | (2006.01) | |
| *G01N 33/68* | (2006.01) | |

(52) U.S. Cl.
CPC .......... *C07K 16/2887* (2013.01); *A61P 13/12* (2018.01); *G01N 33/686* (2013.01); *C07K 2317/24* (2013.01); *C07K 2317/732* (2013.01); *C07K 2317/734* (2013.01); *G01N 2800/24* (2013.01)

(58) Field of Classification Search
None
See application file for complete search history.

(56) References Cited

U.S. PATENT DOCUMENTS

| | | |
|---|---|---|
| 8,361,721 B2 | 1/2013 | Copland et al. |
| 2006/0040293 A1 | 2/2006 | Salonen et al. |
| 2007/0210253 A1 | 9/2007 | Behar et al. |
| 2010/0167285 A1 | 7/2010 | Schreiber et al. |
| 2010/0196426 A1 | 8/2010 | Skog et al. |
| 2013/0280738 A1 | 10/2013 | Salant et al. |
| 2013/0303395 A1 | 11/2013 | Lueking et al. |
| 2017/0216244 A1 | 8/2017 | Tufro |
| 2017/0219580 A1 | 8/2017 | Lambeau et al. |
| 2018/0203020 A1 | 7/2018 | Esnault et al. |
| 2019/0183969 A1 | 6/2019 | Zhu |
| 2020/0088734 A1 | 3/2020 | Lotvall et al. |
| 2021/0270832 A1 | 9/2021 | Charlesworth et al. |
| 2022/0389108 A1 | 12/2022 | Sethi et al. |
| 2023/0314425 A1 | 10/2023 | Sethi et al. |
| 2023/0400465 A1 | 12/2023 | Fervenza et al. |

FOREIGN PATENT DOCUMENTS

| | | |
|---|---|---|
| EP | 2977758 | 1/2016 |
| WO | WO 2008/118969 | 10/2008 |
| WO | WO 2016/012542 | 1/2016 |
| WO | WO 2017/009245 | 1/2017 |
| WO | WO 2018/031947 | 2/2018 |
| WO | WO 2019/030461 | 2/2019 |
| WO | WO 2020/037135 | 2/2020 |
| WO | WO 2021/178863 | 9/2021 |
| WO | WO 2022/103598 | 5/2022 |
| WO | WO 2023/172847 | 9/2023 |

OTHER PUBLICATIONS

Dai et al., Diagnostic accuracy of PLA2R autoantibodies and glomerular staining for the differentiation of idiopathic and secondary membranous nephropathy: an updated meta-analysis, Scientific Reports, (2015), 5(8803), (9 page) (Year: 2015).*

Al-Rabadi et al., "Serine Protease HTRA1 as a Novel Target Antigen in Primary Membranous Nephropathy," J. Am. Soc. Nephrol., Jul. 2021, 32(7):1666-1681.

Bobart et al., "Noninvasive diagnosis of primary membranous nephropathy using phospholipase A2 receptor antibodies," Kidney Int., Feb. 2019, 95(2):429-438.

Caza et al., "Neural cell adhesion molecule 1 is a novel autoantigen in membranous lupus nephritis," Kidney Int., Jul. 2021, 100(1):171-181.

Chang et al., "Spectrum of renal pathology in hematopoietic cell transplantation: a series of 20 patients and review of the literature," Clin. J. Am. Soc. Nephrol., Sep. 2007, 2(5):1014-1023.

(Continued)

*Primary Examiner* — Ellen J Marcsisin
(74) *Attorney, Agent, or Firm* — Fish & Richardson P.C.

(57) ABSTRACT

This document relates to methods and materials involved in identifying and/or treating mammals having membranous nephropathy (e.g., membranous nephropathy with an elevated level of a Semaphorin 3B polypeptide in the glomerular basement membrane (GBM)). For example, methods and materials for administering one or more immunosuppressive agents (e.g., corticosteroids, cyclosporine, or a B-cell reduction or depletion agent such as Rituximab) to treat a mammal (e.g., a human) having membranous nephropathy are provided.

12 Claims, 12 Drawing Sheets

Specification includes a Sequence Listing.

(56)　　　　　References Cited

OTHER PUBLICATIONS

Ciani et al., "Mice Lacking the Giant Protocadherin mFAT1 Exhibit Renal Slit Junction Abnormalities and a Partially Penetrant Cyclopia and Anophthalmia Phenotype," Mol. Cell Biol., May 2003, 23(10):3575-3582.

Extended European Search Report in European Appln. No. 21765020.9, dated Feb. 12, 2024, 11 pages.

Fabretti et al., "Expanding the Spectrum of FAT1 Nephropathies by Novel Mutations That Affect Hippo Signaling," Kidney Int. Rep., May 2021, 6(5):1368-1378.

Feltkamp et al., "Elution of antibodies from biopsy tissue," J. Clin. Pathol., Oct. 1970, 23(7):629-631.

Garred et al., "The IgG subclass pattern of complement activation depends on epitope density and antibody and complement concentration," Scand. J. Immunol., Sep. 1989, 30(3):379-382.

Gee et al., "FAT1 mutations cause a glomerulotubular nephropathy," Nat. Commun., Feb. 2016, 7:10822.

Hiesse et al., "Membranous nephropathy in a bone marrow transplant recipient," Am. J. Kidney Dis., Feb. 1988, 11(2):188-191.

Hu, "The role of graft-versus-host disease in haematopoietic cell transplantation-associated glomerular disease," Nephrol. Dial. Transplant., Jun. 2011, 26(6):2025-2031.

Inoue et al., "FAT is a component of glomerular slit diaphragms," Kidney Int., Mar. 2001, 59(3):1003-1012.

Kudose et al., "NELL1-Associated Membranous Glomerulopathy After Hematopoietic Stem Cell Transplantation," Kidney Int. Rep., Jul. 2021, 6(7):1992-1995.

Mahoney et al., "The fat tumor suppressor gene in *Drosophila* encodes a novel member of the cadherin gene superfamily," Cell, Nov. 1991, 67(5):853-868.

Michaelsen et al., "Human IgG subclass pattern of inducing complement-mediated cytolysis depends on antigen concentration and to a lesser extent on epitope patchiness, antibody affinity and complement concentration," Eur. J. Immunol., Jan. 1991, 21(1):11-16.

Mustjoki et al., "Somatic Mutations in 'Benign' Disease," N. Engl. J. Med., May 2021, 384:2039-2052.

Na et al., "Dissecting the relationships of IgG subclasses and complements in membranous lupus nephritis and idiopathic membranous nephropathy," PLoS One, Mar. 2017, 12(3):e0174501.

Nasr et al., "Membranous Nephropathy With Extensive Tubular Basement Membrane Deposits Following Allogeneic Hematopoietic Cell Transplant: A Report of 5 Cases," Am. J. Kidney Dis., Jun. 2022, 79(6):904-908.

Nergizoglu et al., "Chronic graft-versus-host disease complicated by membranous glomerulonephritis," Nephrol. Dial. Transplant., Oct. 1999, 14(10):2461-2463.

Pronina et al., "Altered expression of the SEMA3B gene in epithelial tumors," Cell Mol. Biol., Jun. 2009, 43(3):403-409.

Sadeqzadeh et al., "Sleeping giants: emerging roles for the fat cadherins in health and disease," Med. Res. Rev., Jan. 2014, 34(1):190-221.

Sato et al., "Nephrotic syndrome in a bone marrow transplant recipient with chronic graft-versus-host disease," Bone Marrow Transplant., Aug. 1995, 16(2):303-305.

Sethi et al., "A proposal for standardized grading of chronic changes in native kidney biopsy specimens," Kidney Int., Apr. 2017, 91(4):787-789.

Sethi et al., "Abstract: PO1467: Hematopoietic Stem Cell Transplant Membranous Nephropathy Is Associated with Protocadherin FAT1," Presented at the American Society of Nephrology Annual Meeting, Nov. 4, 2021, 2 pages.

Sethi et al., "Hematopoietic Stem Cell Transplant-Membranous Nephropathy Is Associated with Protocadherin FAT1," J. Am. Soc. Nephrol., May 2022, 33(5):1033-1044.

Sethi, "Membranous nephropathy: a single disease or a pattern of injury resulting from different diseases," Clin. Kidney J., Mar. 2021, 14(10):2166-2169.

Sethi, "New 'Antigens' in Membranous Nephropathy," J. Am. Soc. Nephrol., Feb. 2021, 32(2):268-278.

Srinivasan et al., "Nephrotic syndrome: an under-recognised immune-mediated complication of non-myeloablative allogeneic haematopoietic cell transplantation," Br. J. Haematol., Oct. 2005, 131(1):74-79.

Steen et al., "The ABC's (and XYZ's) of peptide sequencing," Nat. Rev. Mol. Cell Biol., Sep. 2004, 5(9):699-711.

Suzuki, "Protocadherins and diversity of the cadherin superfamily," J. Cell Sci., Nov. 1996, 109(Pt. 11):2609-2611.

Troxell et al., "Renal pathology associated with hematopoietic stem cell transplantation," Adv. Anat. Pathol., Sep. 2014, 21(5):330-340.

UniProt Accession No. Q14517, "FAT1_HUMAN," Jul. 5, 2017, 9 pages.

Wojtalwicz et al., "A soluble form of the giant cadherin Fat1 is released from pancreatic cancer cells by ADAM10 mediated ectodomain shedding," PLoS One, Mar. 2014, 9(3):e90461.

Yaoita et al., "Role of Fat1 in cell-cell contact formation of podocytes in puromycin aminonucleoside nephrosis and neonatal kidney," Kidney Int., Aug. 2005, 68(2):542-551.

Yorioka et al., "Membranous nephropathy with chronic graft-versus-host disease in a bone marrow transplant recipient," Nephron., Nov. 1998, 80(3):371-372.

Ahn et al., "Cloning of the putative tumour suppressor gene for hereditary multiple exostoses (EXT1)," Nat. Genetics, Oct. 1, 1995, 11(2):137-143.

Alarcón, "Multiethnic lupus cohorts: what have they taught us?," Reumatol. Clinica, Dec. 23, 2010, 7(1):3-6.

Almaani et al., "Update on Lupus Nephritis," Clin. J. Am. Soc. Nephrology, Nov. 7, 2016, 12(5):825-835.

Alto et al., "Semaphorins and their Signaling Mechanisms," Methods Mol. Biology, Oct. 28, 2016, 1493:1-25.

Altschul et al., "Gapped BLAST and PSI-BLAST: a new generation of protein database search programs," Nucleic Acids Research, Sep. 1, 1997, 25(17):3389-3402.

Anders, "Nephropathic autoantigens in the spectrum of lupus nephritis," Nat. Rev. Nephrology, Jun. 13, 2019, 15(10):595-596.

Aoki et al., "The reduction of heparan sulphate in the glomerular basement membrane does not augment urinary albumin excretion," Nephrol. Dial. Transplantation, Jan. 1, 2018, 33(1):26-33.

Bajema et al., "Revision of the International Society of Nephrology/Renal Pathology Society classification for lupus nephritis: clarification of definitions, and modified National Institutes of Health activity and chronicity indices," Kidney International, Apr. 1, 2018, 93(4):789-796.

Bech et al., "Association of Anti-PLA2R Antibodies with Outcomes after Immunosuppressive Therapy in Idiopathic Membranous Nephropathy," Clin. J. Am. Soc. Nephrology, Aug. 7, 2014, 9(8):1386-1392.

Beck Jr. et al., "Membranous nephropathy: from models to man," J. Clin. Investigation, Jun. 2, 2014, 124(6):2307-2314.

Beck Jr. et al., "M-type phospholipase A2 receptor as target antigen in idiopathic membranous nephropathy," N. Engl. J. Medicine, Jul. 2, 2009, 361(1):11-21.

Beck Jr. et al., "Rituximab-Induced Depletion of Anti-PLA2R Autoantibodies Predicts Response in Membranous Nephropathy," J. Am. Soc. Nephrology, Jul. 22, 2011, 22(8):1543-1550.

Bertelli et al., "Molecular and Cellular Mechanisms for Proteinuria in Minimal Change Disease," Front. Medicine, Jun. 11, 2018, 5:170, 13 pages.

Bobart et al., "A Target Antigen-Based Approach to the Classification of Membranous Nephropathy," Mayo Clin. Proceedings, Mar. 2021, 96(3):577-591.

Borza, "Glomerular basement membrane heparan sulfate in health and disease: A regulator of local complement activation," Matrix Biology, Sep. 6, 2016, 57-58:299-310.

Brasch et al., "Thinking outside the cell: how cadherins drive adhesion," Trends Cell Biology, May 1, 2012, 22(6):299-310.

Busse et al., "Contribution of EXT1, EXT2, and EXTL3 to Heparan Sulfate Chain Elongation," J. Biol. Chemistry, Nov. 9, 2007, 282(45):32802-32810.

Busse et al., "In Vitro Polymerization of Heparan Sulfate Backbone by the EXT Proteins," J. Biol. Chemistry, Oct. 17, 2003, 278(42):41333-41337.

Busse-Wicher et al., "The extostosin family: Proteins with many functions," Matrix Biology, Apr. 2014, 35:25-33.

(56) References Cited

OTHER PUBLICATIONS

Chen et al., "Glomerular basement membrane and related glomerular disease," Transl. Research, Oct. 2012, 160(4):291-297.

Chen et al., "Loss of heparan sulfate glycosaminoglycan assembly in podocytes does not lead to proteinuria," Kidney International, Aug. 2008, 74(3):289-299.

Chen et al., "Podocytes require the engagement of cell surface heparan sulfate proteoglycans for adhesion to extracellular matrices," Kidney International, Dec. 1, 2010, 78(11):1088-1099.

Cook et al., "Genetic Heterogeneity in Families with Hereditary Multiple Exostoses," Am. J. Hum. Genetics, Jul. 1993, 53(1):71-79.

Couser, "Primary Membranous Nephropathy," Clin. J. Am. Soc. Nephrology, May 26, 2017, 12(6):983-997.

De Vriese et al., "A Proposal for a Serology-Based Approach to Membranous Nephropathy," J. Am. Soc. Nephrology, Oct. 24, 2016, 28(2):421-430.

Du et al., "Elevated semaphorin5A in systemic lupus erythematosus is in association with disease activity and lupus nephritis," Clin. Exp. Immunology, Feb. 17, 2017, 188(2):234-242.

Duncan et al., "The link between heparan sulfate and hereditary bone disease: finding a function for the EXT family of putative tumor suppressor proteins," J. Clin. Investigation, Aug. 2001, 108(4):511-516.

Fervenza et al., "Rituximab or Cyclosporine in the Treatment of Membranous Nephropathy," N. Engl. J. Medicine, Jul. 4, 2019, 381(1):36-46.

Frank et al., "Protocadherins," Curr. Opin. Cell Biology, Oct. 2002, 14(5):557-562.

Guan et al., "Autocrine class 3 semaphorin system regulates slit diaphragm proteins and podocyte survival," Kidney International, May 2006, 69(9):1564-1569.

Halbleib et al., "Cadherins in development: cell adhesion, sorting, and tissue morphogenesis," Genes Development, Dec. 1, 2006, 20(23):3199-3214.

Hanset et al., "Podocyte Antigen Staining to Identify Distinct Phenotypes and Outcomes in Membranous Nephropathy: A Retrospective Multicenter Cohort Study," Am. J. Kidney Diseases, Jul. 12, 2020, 76(5):624-635.

Hasebe et al., "Efficient Production and Characterization of Recombinant Human NELL1 Protein in Human Embryonic Kidney 293-F Cells," Mol. Biotechnology, Aug. 5, 2011, 51(1):58-66.

Hasebe et al., "The C-terminal region of NELL1 mediates osteoblastic cell adhesion through integrin α3β1," FEBS Letters, Jun. 20, 2012, 586(16):2500-2506.

Herwig et al., "Thrombospondin Type 1 Domain-Containing 7A Localizes to the Slit Diaphragm and Stabilizes Membrane Dynamics of Fully Differentiated Podocytes," J. Am. Soc. Nephrology, Apr. 10, 2019, 30(5):824-839.

Hihara et al., "Anti-Phospholipase A2 Receptor (PLA2R) Antibody and Glomerular PLA2R Expression in Japanese Patients with Membranous Nephropathy," PLoS One, Jun. 29, 2016, 11(6):e0158154, 12 pages.

Huong et al., "Renal involvement in systemic lupus erythematosus. A study of 180 patients from a single center," Medicine (Baltimore), May 1999, 78(3):148-166.

Itakura et al., "Heparan sulfate is a clearance receptor for aberrant extracellular proteins," J. Cell Biology, Mar. 2, 2020, 19(3):e201911126.

Iwakura et al., "Primary Membranous Nephropathy with Enhanced Staining of Exostosin 1/Exostosin 2 in the Glomeruli: A Report of 2 Cases," Kidney Medicine, May 31, 2021, 3(4):669-673.

Kanwar et al., "Contribution of Proteoglycans Towards the Integrated Functions of Renal Glomerular Capillaries: A Historical Perspective," Am. J. Pathology, Jul. 2007, 171(1):9-13.

Kuroda et al., "Biochemical Characterization and Expression Analysis of Neural Thrombospondin-1-like Proteins NELL1 and NELL2," Biochem. Biophys. Res. Communications, Nov. 1999, 265(1):79-86.

Lee et al., "Overall and cause-specific mortality in systemic lupus erythematosus: an updated meta-analysis," Lupus, Jan. 24, 2016, 25(7):727-734.

Luce et al., "The neuronal EGF-related genes NELL1 and NELL2 are expressed in hemopoietic cells and developmentally regulated in the B lineage," Gene, Apr. 29, 1999, 231(1-2):121-126.

Makker et al., "Idiopathic membranous nephropathy: an autoimmune disease," Semin. Nephrology, Jul. 2011, 31(4):333-340.

Matshuhashi et al., "New gene, nel, encoding a M(r) 93 K protein with EGF-like repeats is strongly expressed in neural tissues of early stage chick embryos," Dev. Dynamics, Jun. 1995, 203(2):212-222.

McCarthy et al., "The Glomerular Basement Membrane as a Model System to Study the Bioactivity of Heparan Sulfate Glycosaminoglycans," Microsc. Microanalysis, Feb. 2012, 18(1):3-21.

McCormick et al., "The putative tumor suppressors EXT1 and EXT2 form a stable complex that accumulates in the Golgi apparatus and catalyzes the synthesis of heparan sulfate," Proc. Natl. Acad. Sci. USA, Jan. 18, 2000, 97(2):668-673.

Miner, "Glomerular basement membrane composition and the filtration barrier," Pediatr. Nephrology, Feb. 15, 2011, 26(9):1413-1417.

Miner, "Glomerular filtration: the charge debate charges ahead," Kidney International, Aug. 2008, 74(3):259-261.

Miner, "The glomerular basement membrane," Exp. Cell Research, Mar. 5, 2012, 318(9):973-978.

Morishita et al., "Protocadherin family: diversity, structure, and function," Curr. Opin. Cell Biology, Oct. 23, 2007, 19(5):584-592.

Nakamura et al., "Expression and regulatory effects on cancer cell behavior of NELL1 and NELL2 in human renal cell carcinoma," Cancer Science, Mar. 26, 2015, 106(5):656-664.

Nesvizhskii et al., "A Statistical Model for Identifying Proteins by Tandem Mass Spectrometry," Anal. Chemistry, Jul. 15, 2003, 75(17):4646-4658.

Neufeld et al., "The semaphorins and their receptors as modulators of tumor progression," Drug Resist. Updates, Aug. 28, 2016, 29:1-12.

Paulson et al., "Glycosyltransferases: Structure, localization, and control of cell type-specific glycosylation," J. Biol. Chemistry, Oct. 15, 1989, 264(3):17615-17618.

PCT International Preliminary Report on Patentability in International Appln. No. PCT/US2021/021170, mailed on Sep. 15, 2022, 9 pages.

PCT International Search Report and Written Opinion in International Appln. No. PCT/US2021/021170, mailed on Jul. 12, 2021, 12 pages.

Pourcine et al., "Prognostic value of PLA2R autoimmunity detected by measurement of anti-PLA2R antibodies combined with detection of PLA2R antigen in membranous nephropathy: A single-centre study over 14 years," PLoS One, Mar. 3, 2017, 12(3):e0173201, 18 pages.

Pozdzik et al., "Membranous Nephropathy and Anti-Podocytes Antibodies: Implications for the Diagnostic Workup and Disease Management," BioMed Res. International, Jan. 8, 2018, 2018:6281054, 19 pages.

ProteinAtlas.org [online], "NELL1—Kidney," available on or before Feb. 9, 2021 via Internet Archive: Wayback Machine URL<https://web.archive.org/web/20210209071800/https://www.proteinatlas.org/ENSG00000165973-NELL1/tissue/kidney>, retrieved on Jun. 4, 2021, retrieved from URL<https://www.proteinatlas.org/ENSG00000165973-NELL1/tissue/kidney>, 3 pages.

ProteinAtlas.org [online], "PCDH7—Kidney," available on or before Jun. 26, 2015 via Internet Archive: Wayback Machine URL<https://web.archive.org/web/20150626215650/https://www.proteinatlas.org/ENSG00000169851-PCDH7/tissue/kidney>, retrieved on Jun. 11, 2021, retrieved from URL<https://www.proteinatlas.org/ENSG00000169851-PCDH7/tissue/kidney>, 3 pages.

Prunotto et al., "Autoimmunity in membranous nephropathy targets aldose reductase and SOD2," J. Am. Soc. Nephrology, Mar. 2010, 21(3):507-519.

Raats et al., "Glomerular heparan sulfate alterations: Mechanisms and relevance for proteinuria," Kidney International, Feb. 2000, 57(2):385-400.

(56) References Cited

OTHER PUBLICATIONS

Ravindran et al., "In Patients with Membranous Lupus Nephritis, Exostosin-Positivity and Exostosin-Negativity Represent Two Different Phenotypes," J. Am. Soc. Nephrology, Jan. 21, 2021, 32(3):695-706.

Ravindran et al., "Proteomic Analysis of Complement Proteins in Membranous Nephropathy," Kidney Int. Reports, Jan. 30, 2020, 5(5):618-626.

Roberts et al., "Familial Nephropathy and Multiple Exostoses With Exostosin-1 (EXT1) Gene Mutation," J. Am. Soc. Nephrology, Mar. 2008, 19(3):450-453.

Ronco et al., "Pathogenesis of membranous nephropathy: recent advances and future challenges," Nat. Rev. Nephrology, Feb. 28, 2012, 8(4):203-213.

Ronco et al., "Pathophysiological advances in membranous nephropathy: time for a shift in patient's care," Lancet, May 16, 2015, 385(9981):1983-1992.

Rops et al., "Modulation of heparan sulfate in the glomerular endothelial glycocalyx decreases leukocyte influx during experimental glomerulonephritis," Kidney International, Apr. 23, 2014, 86(5):932-942.

Rosini et al., "Thrombospondin-1 promotes matrix homeostasis by interacting with collagen and lysyl oxidase precursors and collagen cross-linking sites," Sci. Signaling, May 29, 2018, 11(532):eaar2566, 16 pages.

Sano et al., "Protocadherins: a large family of cadherin-related molecules in central nervous system," EMBO Journal, Jun. 1993, 12(6):2249-2256.

Sethi et al., "Exostosin 1/Exostosin 2-Associated Membranous Nephropathy," J. Am. Soc. Nephrology, May 6, 2019, 30(6):1123-1136.

Sethi et al., "Mass Spectrometry Based Proteomic Diagnosis of Renal Immunoglobulin Heavy Chain Amyloidosis," Clin. J. Am. Soc. Nephrology, Sep. 28, 2010, 5(12):2180-2187.

Sethi et al., "Mass spectrometry based proteomics in the diagnosis of kidney disease," Curr. Opin. Nephrol. Hypertension, May 2013, 22(3):273-280.

Sethi et al., "Neural epidermal growth factor-like 1 protein (NELL-1) associated membranous nephropathy," Kidney International, Oct. 10, 2019, 97(1):163-174.

Sethi et al., "Protocadherin 7-Associated Membranous Nephropathy," J. Am. Soc. Nephrology, Apr. 8, 2021, 32(5):1249-1261.

Sethi et al., "Semaphorin 3B-associated membranous nephropathy is a distinct type of disease predominantly present in pediatric patients," Kidney International, Nov. 1, 2020, 98(5):1253-1264.

Stoddard et al., "Structure and function insights garnered from in silico modeling of the thrombospondin type-1 domain-containing 7A antigen," Proteins, Dec. 21, 2018; 87(2):136-145.

Stojan et al., "Epidemiology of systemic lupus erythematosus: an update," Curr. Opin. Rheumatology, Mar. 2018, 30(2):144-150.

Sugar et al., "N-sulfation of heparan sulfate is critical for syndecan-4-mediated podocyte cell-matrix interactions," Am. J. Physiol. Renal Physiology, Mar. 2, 2016, 310(1):F1123-F1135.

Sugar et al., "Podocyte-specific deletion of NDST1, a key enzyme in the sulfation of heparan sulfate glycosaminoglycans, leads to abnormalities in podocyte organization in vivo," Kidney International, Aug. 7, 2013, 85(2):307-318.

Takamatsu et al., "Diverse roles for semaphorin-plexin signaling in the immune system," Trends Immunology, Feb. 9, 2012, 33(3):127-135.

Tapia et al., "Semaphorin3a disrupts podocyte foot processes causing acute proteinuria," Kidney International, Dec. 12, 2007, 73(6):733-740.

Ting et al., "Human NELL-1 Expressed in Unilateral Coronal Synostosis," J. Bone Miner. Research, Jan. 1999, 14(1): 80-89.

Tomas et al., "Autoantibodies against thrombospondin type 1 domain-containing 7A induce membranous nephropathy," J. Clin. Investigation, May 23, 2016, 126(7):2519-2532.

Tomas et al., "Thrombospondin Type-1 Domain-Containing 7A in Idiopathic Membranous Nephropathy," N. Engl. J. Medicine, Nov. 13, 2014, 371(24):2277-2287.

UniProt Accession No. O60245, "Protocadherin-7," dated Jun. 7, 2017, 5 pages.

Van den Born et al., "Distribution of GBM heparan sulfate proteoglycan core protein and side chains in human glomerular diseases," Kidney International, Feb. 1993, 43(2):454-463.

Vrana et al., "Classification of amyloidosis by laser microdissection and mass spectrometry based proteomic analysis in clinical biopsy specimens," Blood, Oct. 1, 2009, 114(24):4957-4959.

Watanabe et al., "Cloning and Characterization of Two Novel Human cDNAs (NELL1 and NELL2) Encoding Proteins with Six EGF-like Repeats," Genomics, Dec. 15, 1996, 38(3):273-276.

Yazdani et al., "The semaphorins," Genome Biology, Mar. 30, 2006, 7(3):211, 14 pages.

Zaghrini et al., "Novel ELISA for thrombospondin type 1 domain-containing 7A autoantibodies in membranous nephropathy," Kidney International, Mar. 2019, 95(3):666-679.

Zhang et al., "Craniosynostosis in transgenic mice overexpressing Nell-1," J. Clin. Investigation, Sep. 2002, 110(6):861-870.

Zhang et al., "Overexpression of Nell-1, a Craniosynostosis-Associated Gene, Induces Apoptosis in Osteoblasts During Craniofacial Development," J. Bone Miner. Research, Dec. 2003, 18(12):2126-2134.

Zhang et al., "The Role of NELL-1, a Growth Factor Associated with Craniosynostosis, in Promoting Bone Regeneration," J. Dent. Research, Jul. 20, 2010, 89(9):865-878.

U.S. Appl. No. 17/254,086, filed Dec. 18, 2020, M. Cristine Charlesworth, Published as U.S. Patent Application Publication No. 2021/0270832.

U.S. Appl. No. 17/642,773, filed Mar. 14, 2022, Sanjeev Sethi, Pending.

* cited by examiner

Bio View:
1850 Proteins in 1674 Clusters
With 1849 Filtered Out

Probability Legend:
- over 95%
- *80% to 94%*
- 50% to 79%
- 20% to 49%
- 0% to 19%

| | | Accession Number |
|---|---|---|
| Semaphorin-3B OS=Homo sapiens OX=9606 GN=SEMA3B PE=2 SV=1 | | sp | Q13214 | SEM3B_HUMAN |
| Immunoglobulin gamma-1 heavy chain OS=Home sapiens OX=9606 PE=1 SV... | | sp | P0DOX5 | IGG1_HUMAN |
| Immunoglobulin heavy constant gamma 2 OS=Homo sapiens OX=9606 GN=I... | | sp | P01859 | IGHG2_HUMAN |
| Immunoglobulin heavy constant gamma 3 OS=Homo sapiens OX=9606 GN=I... | | sp | P01860 | IGHG3_HUMAN |
| Immunoglobulin heavy constant gamma 4 OS=Homo sapiens OX=9606 GN=I... | | sp | P01861 | IGHG4_HUMAN |
| Secretory phospholipase A2 receptor OS=Homo sapiens OX=9606 GN=PLA2R1... | | sp | Q13018 | PLA2R_HUMAN |

| Molecular Weight | Case 01 | Case 02 | Case 03 |
|---|---|---|---|
| 83 kDa | 19 | 42 | 11 |
| 49 kDa | 25 | 29 | 21 |
| 36 kDa | 24 | 18 | 28 |
| 41 kDa | 20 | 19 | 36 |
| 36 kDa | 20 | 11 | 21 |
| 169 kDa | 2 | 5 | (0) |

FIG. 2A sp|Q13214|SEM3B_HUMAN (100%), 83,121.5 Da

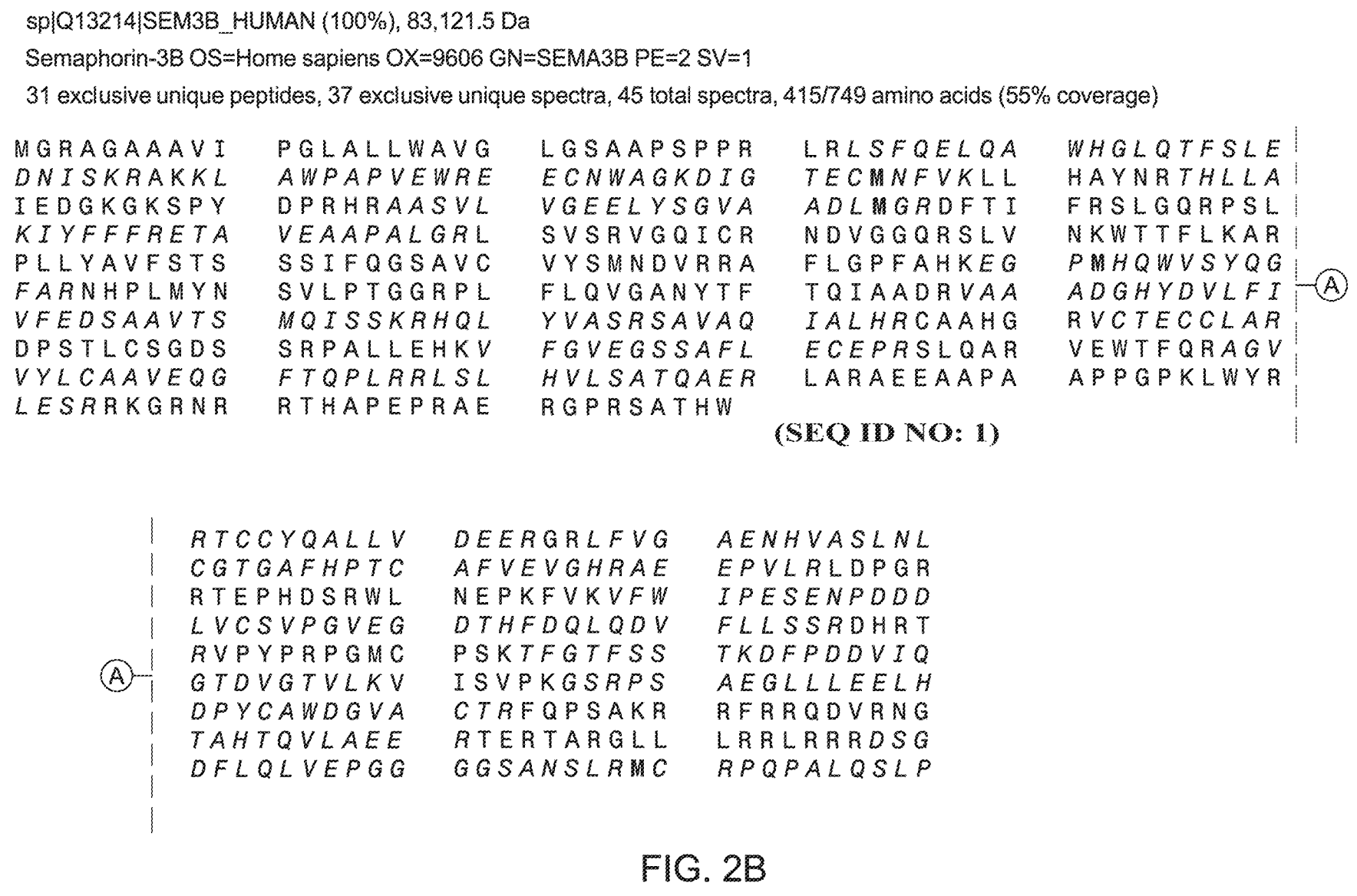

Semaphorin-3B OS=Home sapiens OX=9606 GN=SEMA3B PE=2 SV=1

31 exclusive unique peptides, 37 exclusive unique spectra, 45 total spectra, 415/749 amino acids (55% coverage)

```
MGRAGAAAVI  PGLALLWAVG  LGSAAPSPPR  LRLSFQELQA  WHGLQTFSLE
DNISKRAKKL  AWPAPVEWRE  ECNWAGKDIG  TECMNFVKLL  HAYNRTHLLA
IEDGKGKSPY  DPRHRAASVL  VGEELYSGVA  ADLMGRDFTI  FRSLGQRPSL
KIYFFRETA   VEAAPALGRL  SVSRVGQICR  NDVGGQRSLV  NKWTTFLKAR
PLLYAVFSTS  SSIFQGSAVC  VYSMNDVRRA  FLGPFAHKEG  PMHQWVSYQG
FARNHPLMYN  SVLPTGGRPL  FLQVGANYTF  TQIAADRVAA  ADGHYDVLFI
VFEDSAAVTS  MQISSKRHQL  YVASRSAVAQ  IALHRCAAHG  RVCTECCLAR
DPSTLCSGDS  SRPALLEHKV  FGVEGSSAFL  ECEPRSLQAR  VEWTFQRAGV
VYLCAAVEQG  FTQPLRRLSL  HVLSATQAER  LARAEEAAPA  APPGPKLWYR
LESRRKGRNR  RTHAPEPRAE  RGPRSATHW
```

(SEQ ID NO: 1)

```
RTCCYQALLV  DEERGRLFVG  AENHVASLNL
CGTGAFHPTC  AFVEVGHRAE  EPVLRLDPGR
RTEPHDSRWL  NEPKFVKVFW  IPESENPDDD
LVCSVPGVEG  DTHFDQLQDV  FLLSSRDHRT
RVPYPRPGMC  PSKTFGTFSS  TKDFPDDVIQ
GTDVGTVLKV  ISVPKGSRPS  AEGLLEELH
DPYCAWDGVA  CTRFQPSAKR  RFRRQDVRNG
TAHTQVLAEE  RTERTARGLL  LRRLRRRDSG
DFLQLVEPGG  GGSANSLRMC  RPQPALQSLP
```

FIG. 2B

Semaphorin 3B        IgG        Merged
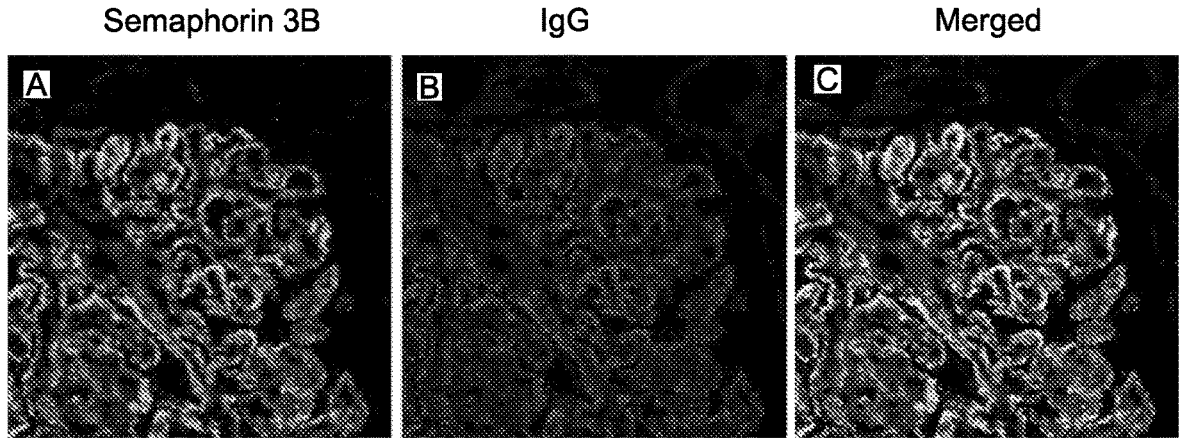
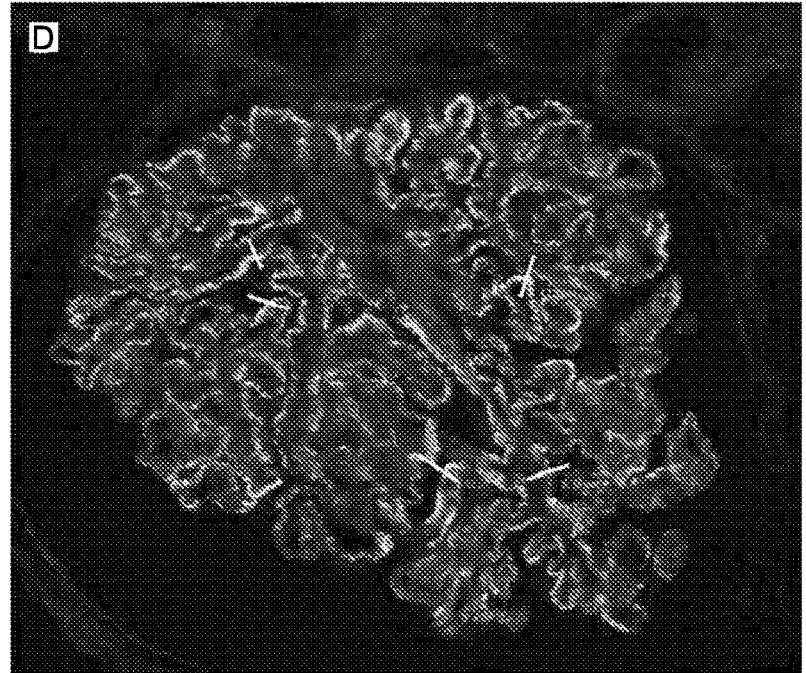
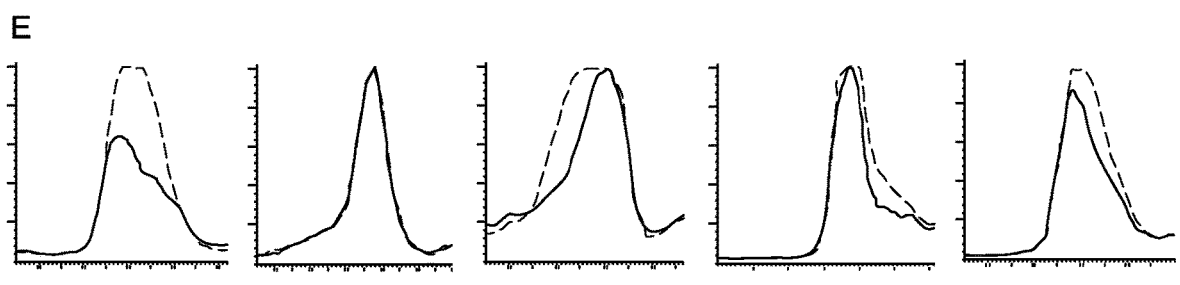
FIG. 7

METHODS AND MATERIALS FOR IDENTIFYING AND TREATING MEMBRANOUS NEPHROPATHY BASED ON ELEVATED SEMAPHORIN 3B

CROSS-REFERENCE TO RELATED APPLICATIONS

This application is a National Stage application under 35 U.S.C. § 371 of International Application No. PCT/US2021/021170, having an International Filing Date of Mar. 5, 2021, which claims the benefit of U.S. Provisional Application Ser. No. 62/986,224, filed Mar. 6, 2020. The disclosure of the prior application is considered part of (and is incorporated by reference in) the disclosure of this application.

SEQUENCE LISTING

This application contains a Sequence Listing that has been submitted electronically as an XML file named "07039-1960US1.XML." The XML file, created on Jul. 5, 2022, is 4 bytes in size. The material in the XML file is hereby incorporated by reference in its entirety.

BACKGROUND

1. Technical Field

This document relates to methods and materials involved in identifying and/or treating mammals having membranous nephropathy (e.g., membranous nephropathy with an elevated level of a Semaphorin 3B polypeptide in the glomerular basement membrane (GBM)). For example, this document provides methods and materials for administering one or more immunosuppressive agents (e.g., corticosteroids, cyclosporine, or a B-cell reduction or depletion agent such as Rituximab) to treat a mammal (e.g., a human) having membranous nephropathy.

2. Background Information

Membranous nephropathy (MN) is the most common cause of nephrotic syndrome in Caucasian adults. It is caused by autoantibodies against target antigens in the glomerular basement membrane (GBM), and is characterized by antigen-antibody complexes that form deposits along the GBM. MN can be classified based on the target antigens phospholipase $A_2$ receptor 1 (PLA2R) and thrombospondin type-1 domain-containing protein 7A (THSD7A). For example, MN can be classified as PLA2R-positive (70%), THSD7A-positive (1-5%), or PLA2R/THSD7A-double negative MN. In the PLA2R/THSD7A-double negative cases, the target antigen(s) remain elusive.

SUMMARY

This document provides methods and materials involved in identifying and/or treating mammals (e.g., humans) having membranous nephropathy (e.g., membranous nephropathy with an elevated level of a Semaphorin 3B polypeptide in the GBM). For example, this document provides methods and materials for identifying a mammal (e.g., a human) having membranous nephropathy having an elevated level of a Semaphorin 3B polypeptide in the GBM that can serve as a target antigen in membranous nephropathy. This document also provides methods and materials for identifying a mammal (e.g., a human) having membranous nephropathy that includes the presence of autoantibodies having binding specificity for a Semaphorin 3B polypeptide. As described herein, mammals (e.g., humans) having membranous nephropathy can be identified as having an elevated level of a Semaphorin 3B polypeptide in the GBM. In such cases, the mammal can be classified as having membranous nephropathy that includes an elevated level of a Semaphorin 3B polypeptide in the GBM. As also described herein, mammals (e.g., humans) having membranous nephropathy can be identified as having autoantibodies having binding specificity for a Semaphorin 3B polypeptide. In such cases, the mammal can be classified as having membranous nephropathy that includes the presence of autoantibodies having binding specificity for a Semaphorin 3B polypeptide. Identifying mammals (e.g., humans) as having membranous nephropathy that includes an elevated level of a Semaphorin 3B polypeptide in the GBM and/or that includes the presence of autoantibodies having binding specificity for a Semaphorin 3B polypeptide can allow clinicians and patients to proceed with appropriate membranous nephropathy treatment options.

This document also provides methods and materials for treating membranous nephropathy. For example, a mammal (e.g., a human) having membranous nephropathy that was identified as having an elevated level of a Semaphorin 3B polypeptide in the GBM, as having autoantibodies having binding specificity for a Semaphorin 3B polypeptide, or as having both an elevated level of a Semaphorin 3B polypeptide in the GBM and autoantibodies having binding specificity for a Semaphorin 3B polypeptide can be administered one or more immunosuppressive agents (e.g., corticosteroids, cyclosporine, or a B-cell reduction or depletion agent such as Rituximab) to reduce inflammation and/or B-cell autoantibody production. As described herein, mammals (e.g., humans) having membranous nephropathy and identified as having an elevated level of a Semaphorin 3B polypeptide in the GBM and/or as having autoantibodies having binding specificity for a Semaphorin 3B polypeptide have a form of membranous nephropathy that is caused by the presence of antigen-autoantibody complexes where the antigen is a Semaphorin 3B polypeptide. In such cases, the mammal (e.g., human) can be effectively treated using one or more immunosuppressive agents (e.g., corticosteroids, cyclosporine, or a B-cell reduction or depletion agent such as Rituximab) to reduce inflammation and/or B-cell autoantibody production. Having the ability to administer one or more immunosuppressive agents to mammals (e.g., humans) (a) having membranous nephropathy and (b) identified as having an elevated level of a Semaphorin 3B polypeptide in the GBM and/or as having autoantibodies having binding specificity for a Semaphorin 3B polypeptide can allow clinicians and patients to treat membranous nephropathy effectively.

As also described herein, most, if not all, membranous nephropathy cases in humans are caused by autoantibodies having specificity to a polypeptide that accumulates in the GBM. Those polypeptides include Semaphorin 3B, neural epidermal growth factor (EGF)-like 1 (NELL-1), exostosin 1 (EXT1), exostosin 2 (EXT2), PLA2R, and THSD7A. In general, the use of immunosuppressive agents such as B-cell reduction or depletion agents (e.g., Rituximab) in cases such as membranous nephropathy currently requires an identification of autoantibodies (e.g., anti-PLA2R autoantibodies or anti-THSD7A autoantibodies) before a powerful B-cell reduction or depletion agent such as Rituximab can be administered to a human to treat membranous nephropathy. Based, at least in part, on the results presented herein, however, such an identification is no longer needed prior to using an immunosuppressive agent to treat membranous nephropathy. For example, a mammal (e.g., a human) having membranous nephropathy (e.g., membranous nephropathy with an elevated level of a Semaphorin 3B, a NELL-1, an EXT1, an EXT2, a PLA2R, and/or a THSD7A polypeptide) can be administered one or more immunosuppressive agents (e.g., corticosteroids, cyclosporine, or a B-cell reduction or depletion agent such as Rituximab) to treat membranous nephropathy without having been tested for an elevated level of any polypeptide in the GBM and without having been tested for the presence of any autoantibody. In some cases, a mammal (e.g., a human) having membranous nephropathy can be administered one or more immunosuppressive agents (e.g., corticosteroids, cyclosporine, or a B-cell reduction or depletion agent such as Rituximab) to treat membranous nephropathy without having been tested for an elevated level of (a) a Semaphorin 3B polypeptide, (b) a NELL-1 poly-peptide, (c) an EXT1 polypeptide, (d) an EXT2 polypeptide, (e) a PLA2R polypeptide, and (f) a THSD7A polypeptide and without having been tested for the presence of (a) an autoantibody having specificity for a Semaphorin 3B poly-peptide, (b) an autoantibody having specificity for a NELL-1 polypeptide, (c) an autoantibody having specificity for an EXT1 polypeptide, (d) an autoantibody having specificity for an EXT2 polypeptide, (e) an autoantibody having speci-ficity for a PLA2R polypeptide, and (f) an autoantibody having specificity for a THSD7A polypeptide. Having the ability to treat membranous nephropathy without prior test-ing for elevated levels of particular polypeptides in the GBM and without prior testing for the presence of particular autoantibodies can allow clinicians and patients to treat membranous nephropathy safely without the added testing delay or expense.

In some cases, identification of the target antigen and autoantibodies can be involved in the diagnosis and/or management of a mammal (e.g., a human) with membranous nephropathy. For example, a mammal (e.g., a human) having membranous nephropathy (e.g., membranous nephropathy with GBM accumulation of a Semaphorin 3B, NELL-1, EXT1, EXT2, PLA2R, and/or THSD7A polypeptide and the presence of autoantibodies to one or more target antigens) can be administered one or more immunosuppressive agents (e.g., corticosteroids, cyclosporine, or a B-cell reduction or depletion agent such as Rituximab) to treat membranous nephropathy. In some cases, the response to the immuno-suppressive treatment can be monitored for a decrease or complete elimination of the autoantibodies to one or more of a PLA2R, THSD7A, EXT1, EXT2, NELL-1, or Semaphorin 3B polypeptide. In some cases, the response to treatment can be monitored by examining a kidney biopsy for a decrease or elimination of one or more target antigens (e.g., a PLA2R, THSD7A, EXT1, EXT2, NELL-1, or Semaphorin 3B poly-peptide). In some cases, a mammal (e.g., a human) having membranous nephropathy can be administered one or more immunosuppressive agents (e.g., corticosteroids, cyclosporine, or a B-cell reduction or depletion agent such as Rituximab) to treat membranous nephropathy based on the presence of an autoantibody to one or more of a PLA2R, THSD7A, EXT1, EXT2, NELL-1, or Semaphorin 3B poly-peptide in the absence of evaluating a kidney biopsy for an elevated level of a PLA2R, THSD7A, EXT1, EXT2, NELL-1, or Semaphorin 3B polypeptide. Although kidney biopsies showing an accumulation of PLA2R, THSD7A, EXT1, EXT2, NELL-1, and/or Semaphorin 3B polypeptides in GBM may be considered a gold standard for diagnosis of membranous nephropathy, the presence of autoantibodies to a PLA2R, THSD7A, EXT1, EXT2, NELL-1, or Semaphorin 3B polypeptide can be used to identify specific types of membranous nephropathy (e.g., membranous nephropathy associated with accumulation of PLA2R, THSD7A, EXT1, EXT2, NELL-1, or Semaphorin 3B polypeptides) without the need for a kidney biopsy.

In general, one aspect of this document features methods for identifying a mammal as having membranous nephropa-thy including an elevated level of a polypeptide within kidney tissue of the mammal, where the polypeptide is a Semaphorin 3B polypeptide. The methods can include, or consist essentially of, (a) determining the presence or absence of autoantibodies within the mammal, where the autoantibodies are specific for the polypeptide, (b) classify-ing the mammal as having the membranous nephropathy if the autoantibodies are present within the mammal, and (c) classifying the mammal as not having the membranous nephropathy if the autoantibodies are absent within the mammal. The mammal can be a human. The membranous nephropathy can lack an elevated level of a NELL-1 poly-peptide within the kidney tissue and can lack an elevated level of a NELL-1 polypeptide within the kidney tissue. The membranous nephropathy can lack an elevated level of an EXT1 polypeptide within the kidney tissue and can lack an elevated level of an EXT2 polypeptide within the kidney tissue. The membranous nephropathy can lack an elevated level of a PLA2R polypeptide within the kidney tissue. The membranous nephropathy can lack an elevated level of a THSD7A polypeptide within the kidney tissue. The method can include detecting the presence of the autoantibodies and classifying the mammal as having the membranous neph-ropathy. The method can include detecting the absence of the autoantibodies and classifying the mammal as not having the membranous nephropathy.

In another aspect, this document features methods for identifying a mammal as having kidney tissue including an elevated level of a polypeptide, where the polypeptide is a Semaphorin 3B polypeptide. The methods can include, or consist essentially of, (a) determining the presence or absence of the kidney tissue within a sample obtained from the mammal, (b) classifying the mammal as having the kidney tissue if the presence is determined, and (c) classi-fying the mammal as not having the kidney tissue if the absence is determined. The mammal can be a human. The kidney tissue can lack an elevated level of a NELL-1 polypeptide. The kidney tissue can lack an elevated level of an EXT1 polypeptide, and the kidney tissue can lack an elevated level of an EXT2 polypeptide. The kidney tissue can lack an elevated level of a PLA2R polypeptide. The kidney tissue can lack an elevated level of a THSD7A polypeptide. The method can include detecting the presence and classifying the mammal as having the kidney tissue. The method can include detecting the absence and classifying the mammal as not having the kidney tissue.

In another aspect, this document features methods for identifying a mammal having membranous nephropathy as having autoantibodies specific for a polypeptide, where the polypeptide is a Semaphorin 3B polypeptide. The methods can include, or consist essentially of, (a) determining the presence or absence of the autoantibodies within the mam-mal, (b) classifying the mammal as having the autoantibod-ies if the autoantibodies are present within the mammal, and (c) classifying the mammal as not having the autoantibodies if the autoantibodies are absent within the mammal. The mammal can be a human. The kidney tissue of the mammal can lack an elevated level of a NELL-1 polypeptide. The kidney tissue of the mammal can lack an elevated level of an EXT1 polypeptide and can lack an elevated level of an EXT2 polypeptide. The kidney tissue of the mammal can lack an elevated level of a PLA2R polypeptide. The kidney tissue of the mammal can lack an elevated level of a THSD7A polypeptide. The method can include detecting the presence and classifying the mammal as having the autoantibodies. The method can include detecting the absence and classifying the mammal as not having the autoantibodies.

In another aspect, this document features methods for treating a mammal having membranous nephropathy. The methods can include, or consist essentially of, (a) identifying a mammal as having (i) autoantibodies specific for a polypeptide or (ii) kidney tissue comprising an elevated level of the polypeptide, where the polypeptide is a Semaphorin 3B polypeptide, and (b) administering an immunosuppressant to the mammal. The mammal can be a human. The mammal can be identified as having the autoantibodies. The mammal can be identified as having the kidney tissue. The immunosuppressant can be a B-cell inhibitor. The B-cell inhibitor can be rituximab. The immunosuppressant can be a calcineurin inhibitor. The calcineurin inhibitor can be cyclosporine or tacrolimus. The immunosuppressant can be an mTOR inhibitor. The mTOR inhibitor can be sirolimus or everolimus. The immunosuppressant can be a DNA damage inducer. The DNA damage inducer can be chlorambucil. The level of autoantibodies present within the mammal can be reduced by at least 5 percent following the administering step. The level of autoantibodies present within the mammal can be reduced by at least 25 percent following the administering step. The method level of autoantibodies present within the mammal can be reduced by at least 50 percent following the administering step.

In another aspect, this document features methods for treating a mammal having membranous nephropathy. The methods can include, or consist essentially of, administering an immunosuppressant to a mammal identified as having (i) autoantibodies specific for a polypeptide or (ii) kidney tissue comprising an elevated level of the polypeptide, where the polypeptide is a Semaphorin 3B polypeptide. The mammal can be a human. The mammal can be identified as having the autoantibodies. The mammal can be identified as having the kidney tissue. The immunosuppressant can be a B-cell inhibitor. The B-cell inhibitor can be rituximab. The immunosuppressant can be a calcineurin inhibitor. The calcineurin inhibitor can be cyclosporine or tacrolimus. The immunosuppressant can be an mTOR inhibitor. The mTOR inhibitor can be sirolimus or everolimus. The immunosuppressant can be a DNA damage inducer. The DNA damage inducer can be chlorambucil. The level of autoantibodies present within the mammal can be reduced by at least 5 percent following the administering step. The level of autoantibodies present within the mammal can be reduced by at least 25 percent following the administering step. The level of autoantibodies present within the mammal can be reduced by at least 50 percent following the administering step.

In another aspect, this document features methods for treating a mammal having membranous nephropathy and kidney tissue including an elevated level of a polypeptide, where the polypeptide is a Semaphorin 3B polypeptide. The methods can include, or consist essentially of, administering an immunosuppressant to the mammal. The mammal can be a human. The mammal can have autoantibodies specific for the polypeptide. The mammal can be identified as having the kidney tissue. The kidney tissue can lack an elevated level of a NELL-1 polypeptide. The kidney tissue can lack an elevated level of an EXT1 polypeptide. The kidney tissue can lack an elevated level of an EXT2 polypeptide. The kidney tissue can lack an elevated level of a PLA2R polypeptide. The kidney tissue can lack an elevated level of a THSD7A polypeptide. The immunosuppressant can be a B-cell inhibitor. The B-cell inhibitor can be rituximab. The immunosuppressant can be a calcineurin inhibitor. The calcineurin inhibitor can be cyclosporine or tacrolimus. The immunosuppressant can be an mTOR inhibitor. The mTOR inhibitor can be sirolimus or everolimus. The immunosuppressant can be a DNA damage inducer. The DNA damage inducer can be chlorambucil. The level of autoantibodies present within the mammal can be reduced by at least 5 percent following the administering step. The level of autoantibodies present within the mammal can be reduced by at least 25 percent following the administering step. The level of autoantibodies present within the mammal can be reduced by at least 50 percent following the administering step.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 2A and B. Proteomic identification of Sema3B in PLA2R-negative MN. Glomeruli were microdissected and analyzed using mass spectrometry as described herein.

FIG. 2A shows detection of Sema3B in three cases of PLA2R-negative MN. Numbers in boxes on right represent spectral counts of MS/MS matches to a respective protein. Top panel shows spectral counts of Sema3B in the three cases. Panels 2-4 show the immunoglobulins IgG1, IgG2, IgG3, and IgG4, and bottom panel shows baseline spectral counts of PLA2R.

FIG. 2B shows a representative sequence coverage map of Sema3B from one case. Italicized amino acids are the amino acids detected. Note the extensive coverage. Bold text indicated amino acids with artefactual chemical modification induced by mass spectrometry such as oxidation of methionine. The presented amino acid sequence without the artifacts is referred to herein as SEQ ID NO:1.

Figure 3:
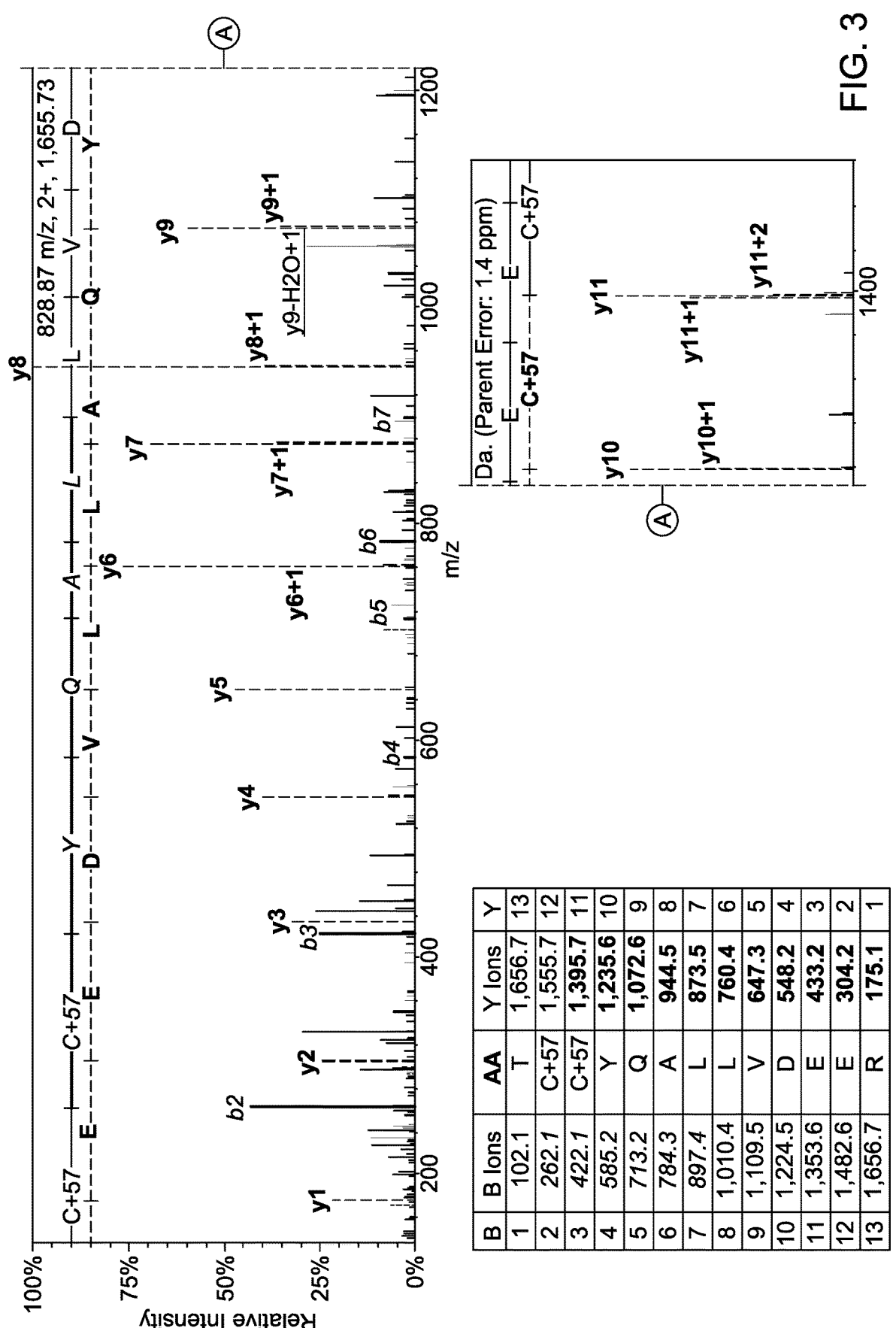

FIG. 3. An example of MS/MS spectra match to a sequence from Sema3B. The figure shows an example of MS/MS spectra of ion 828.87 [M+2H] 2+ corresponding to Semaphorin-3B peptide TCCYQALLVDEER (SEQ ID NO:2).

Figure 4A:
Figure 4B:
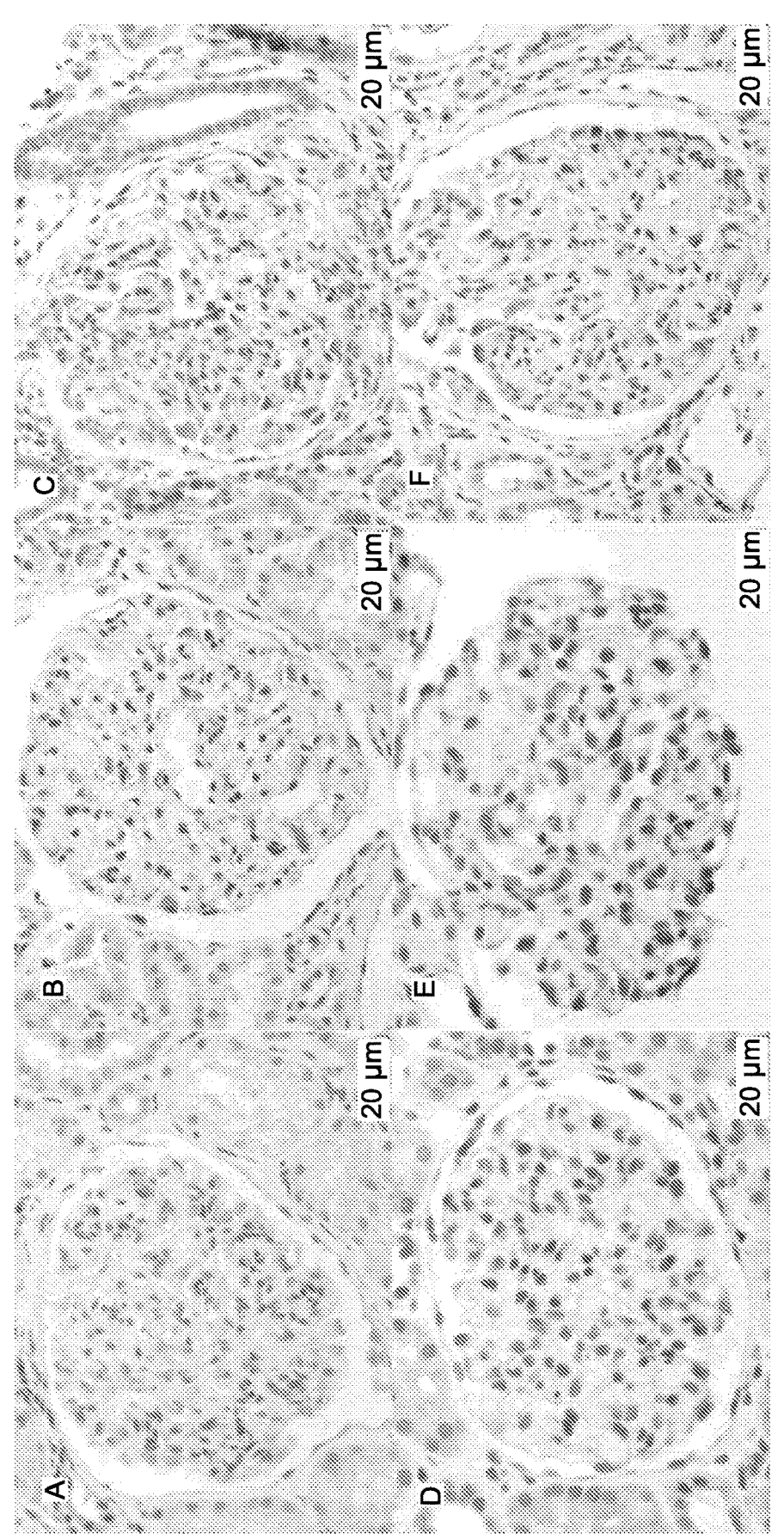

FIGS. 4A and 4B. Immunohistochemical stain for Sema3B in Sema3B-associated MN (Mayo Clinic cohort), PLA2R-associated MN, and control cases. FIG. 4A shows bright granular capillary wall staining for Sema3B along the glomerular basement membranes in three cases of Sema3B-associated MN (Patients 1-3). FIG. 4B shows negative Sema3B staining in a representative case of (panel A) diabetic glomerulosclerosis, (panel B) focal segmental glomerulosclerosis, (panel C) IgA nephropathy, (panel D) minimal change disease, (panel E) time zero transplant biopsy, and (panel F) PLA2R-positive MN.

Figure 5:
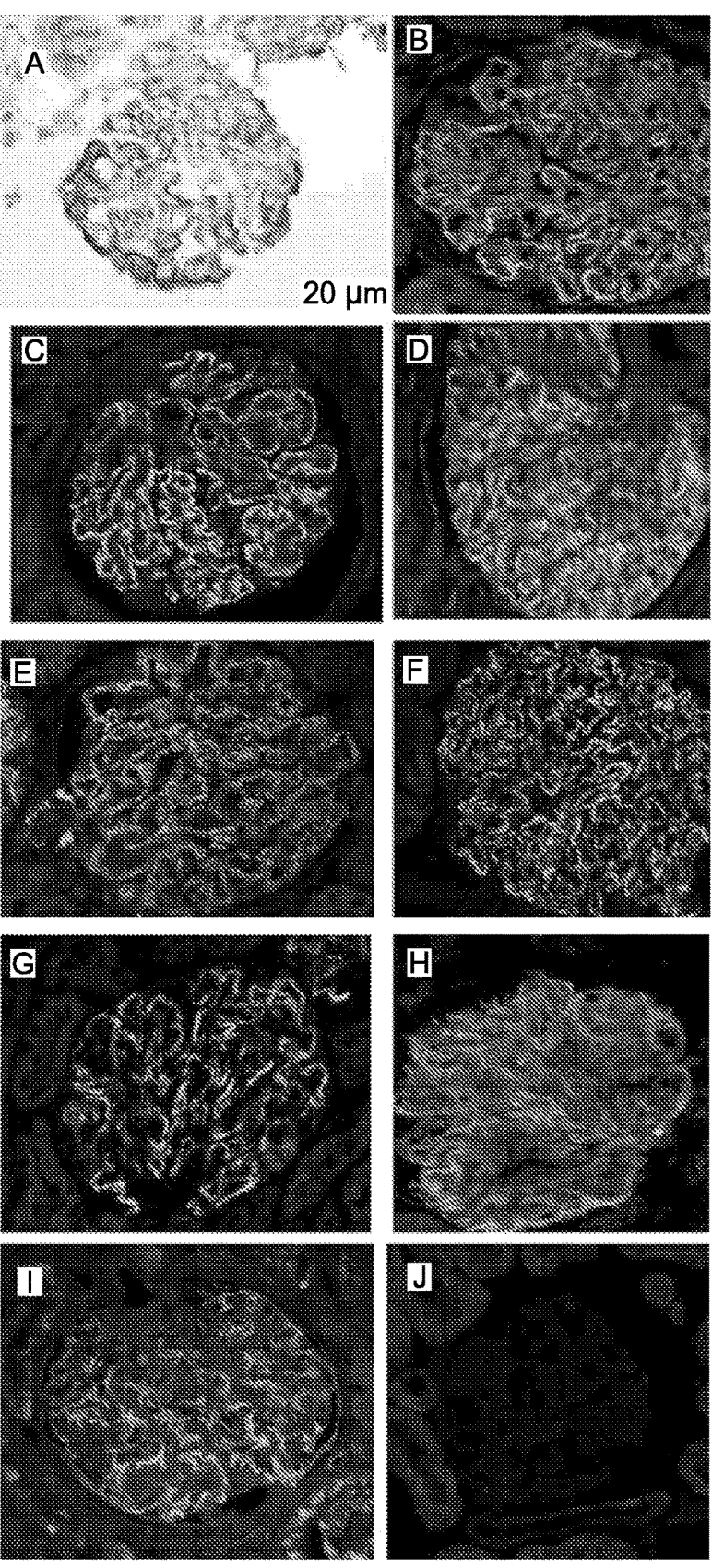

FIGS. 5A-J. Immunofluorescence microscopy for Sema3B in the validation cohorts, showing granular staining for Sema3B. FIGS. 5A and 5B are the same case (patient 4) stained by IHC and IF. FIGS. 5C and 5D are the same patient (patient 5, with biopsies at the ages of 1 and 19). FIGS. 5E-I represent patients 6, 7, 8, 10, and 11. FIG. 5J represents a PLA2R-positive MN control case.

FIGS. 6A-F. IF staining for IgG and Sema3B (patient 5). FIG. 6B is from the archives, and the photomicrograph was taken 20 years ago. It is out of focus and the frozen tissue is no longer available. The paraffin slides for detection of Sema3B were also retrieved from the archives. They were of poor quality, which may explain the unusual staining pattern of Sema3B although it cannot be excluded that it might be more diffuse at the onset of the membranous nephropathy.

FIGS. 7A-E. Detection of Sema3B and IgG in glomerular immune deposits in Sema3B associated MN by confocal immunofluorescence microscopy analysis. Glomeruli were double-labeled with anti-Sema3B (A) and anti-human IgG (B), with the right panel (C) showing the merged image. FIG. 7D shows the enlarged image of the merged image. The white lines show the places where fluorescence was recorded across sections of a representative capillary loop. FIG. 7E shows quantitative analysis of the fluorescence recorded across sections of a representative capillary loop (arrows). Note the superimposition of the two signals, which indicates that subepithelial immune deposits contain Sema3B and IgG.

FIGS. 8A-F. Detection of Sema3B and IgG in glomerular immune deposits by confocal microscopy analysis (patient 6). Glomeruli double-labeled with anti-Sema3B (A) and anti-human IgG (B). FIG. 8C shows the merged image. FIGS. 8D, 8E, and 8F are enlarged images of the boxed areas in FIGS. 8A, 8B, and 8C, respectively.

Figure 9:
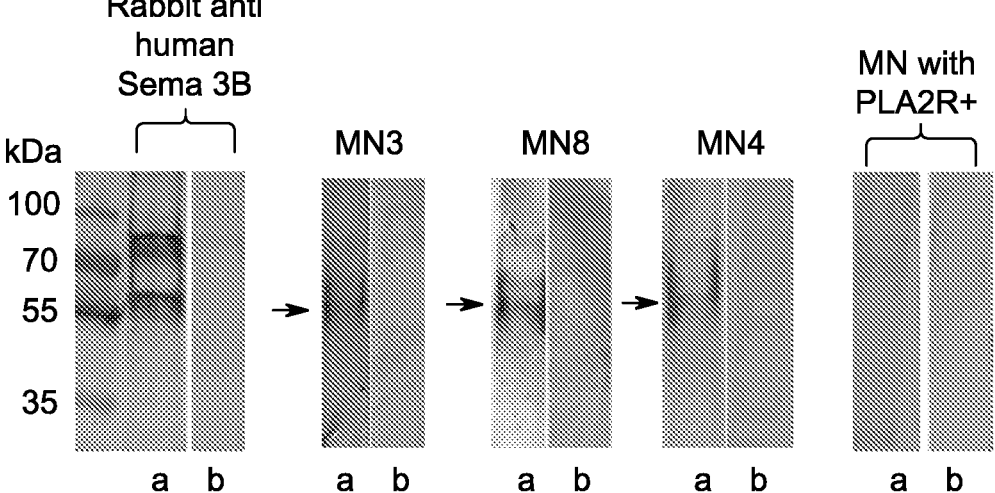

FIG. 9. Detection of anti Sema3B antibodies in the serum by Western blot analysis. Western blotting revealed reactivity of serum samples with (a) overexpression lysate for Sema 3B and (b) empty vector transfected control cell lysate. Patients serum recognized a band at ~55 kDa representing the secreted form of the protein. Note the lack of reactivity of serum from patient with PLA2R associated MN. MN3 represents patient 3, MN4 represents patient 4, and MN8 represents patient 8.

FIGS. 10A-F. Representative kidney biopsy findings (patient 3). FIG. 10A: Light microscopy showing slightly thickened glomerular capillary walls (40×). FIGS. 10B-C: Immunofluorescence microscopy showing glomerular and tubular basement membrane staining for IgG. FIGS. 10D-E: Electron microscopy showing (D) subepithelial and (E) tubular basement membrane deposits. FIG. 10F: Sema3B staining along the glomerular basement membrane. The tubular basement membranes are negative. Arrow points to electron dense deposits (D-9300×, E-4800×).

DETAILED DESCRIPTION

This document provides methods and materials for identifying and/or treating mammals (e.g., humans) having membranous nephropathy (e.g., membranous nephropathy with an elevated level of a Semaphorin 3B polypeptide in the GBM). For example, this document provides methods and materials for identifying a mammal (e.g., a human) having membranous nephropathy as having (a) autoantibodies specific for a Semaphorin 3B polypeptide and/or (b) a GBM having an elevated level of a Semaphorin 3B polypeptide.

Any appropriate mammal having membranous nephropathy can be identified as having (a) autoantibodies specific for a Semaphorin 3B polypeptide and/or (b) kidney tissue (e.g., GBM) having an elevated level of a Semaphorin 3B polypeptide. In some cases, a mammal having membranous nephropathy also can have one or more other diseases or disorders (e.g., a cancer such as a lung cancer or a breast cancer). Examples of mammals having membranous nephropathy that can be identified as having (a) autoantibodies specific for a Semaphorin 3B polypeptide and/or (b) kidney tissue (e.g., GBM) having an elevated level of a Semaphorin 3B polypeptide as described herein include, without limitation, primates (e.g., humans and monkeys), dogs, cats, horses, cows, pigs, sheep, rabbits, mice, and rats. For example, humans having membranous nephropathy can be identified as having (a) autoantibodies specific for a Semaphorin 3B polypeptide and/or (b) kidney tissue such as GBM having an elevated level of a Semaphorin 3B polypeptide as described herein. In some cases, a pediatric human less than 18 years of age (e.g., less than 15, 12, 10, 8, 6, 4, or 2 years of age) having membranous nephropathy can be identified as having (a) autoantibodies specific for a Semaphorin 3B polypeptide and/or (b) kidney tissue such as GBM having an elevated level of a Semaphorin 3B polypeptide as described herein.

Any appropriate method can be used to determine if a mammal (e.g., a human) has autoantibodies specific for a Semaphorin 3B polypeptide. For example, immunological assays using a Semaphorin 3B polypeptide (or a fragment thereof capable of binding to an anti-Semaphorin 3B antibody) can be used to determine if a sample contains autoantibodies specific for a Semaphorin 3B polypeptide. In some cases, an immobilized Semaphorin 3B polypeptide (or an immobilized fragment thereof) can be used to capture an anti-Semaphorin 3B autoantibody if present within a sample being tested, and an anti-Ig antibody (e.g., an anti-human IgG antibody when testing for human autoantibodies) can be used to determine whether or not autoantibodies were captured. In some cases, an anti-Ig antibody can be labeled (e.g., fluorescently or enzymatically labeled) to aid in detection. Any appropriate sample can be used to determine if a mammal (e.g., a human) has autoantibodies specific for a Semaphorin 3B polypeptide. For example, blood samples (e.g., whole blood samples, serum samples, and plasma samples) or urine samples obtained from a mammal being tested can be used to determine if a mammal (e.g., a human) has autoantibodies specific for a Semaphorin 3B polypeptide.

Any appropriate method can be used to determine if a mammal (e.g., a human) has kidney tissue (e.g., GBM)

having an elevated level of a Semaphorin 3B polypeptide. For example, immunological techniques such as immuno-histochemistry (IHC) techniques, immunofluorescence (IF) techniques, or Western blot techniques can be used to determine if a mammal (e.g., a human) has kidney tissue (e.g., GBM) having an elevated level of a Semaphorin 3B polypeptide. In some cases, a kidney tissue sample obtained from a mammal to be tested can be stained using an anti-Semaphorin 3B antibody to determine if the mammal has kidney tissue (e.g., GBM) having an elevated level of Semaphorin 3B polypeptides. Any appropriate sample can be used to determine if a mammal (e.g., a human) has kidney tissue (e.g., GBM) having an elevated level of a Semaphorin 3B polypeptide. For example, kidney tissue biopsies can be obtained from a mammal (e.g., a human) being tested and used to determine if a mammal (e.g., a human) has kidney tissue (e.g., GBM) having a Semaphorin 3B polypeptide.

The term "elevated level" as used herein with respect to a Semaphorin 3B polypeptide level refers to a level of Semaphorin 3B polypeptides present within kidney tissue (e.g., GBM) that is greater (e.g., at least 10, 25, 35, 45, 50, 55, 65, 75, 80, 90, or 100 percent greater) than the median level of Semaphorin 3B polypeptides present within normal kidney tissue (e.g., a normal GBM) of comparable mammals not having membranous nephropathy.

A Semaphorin 3B polypeptide can include any appropriate amino acid sequence. An exemplary amino acid of a Semaphorin 3B polypeptide can include, without limitation, the amino acid sequence set forth in SEQ ID NO:1 (see, e.g., FIG. 2B). In some cases, the amino acid sequence of a Semaphorin 3B polypeptide can have a sequence that deviates from the nucleotide sequence set forth in SEQ ID NO:1, sometimes referred to as a variant sequence. For example, a Semaphorin 3B polypeptide can have an amino acid sequence that includes one or more modifications (e.g., deletions, insertions, and substitutions) to the amino acid sequence set forth in SEQ ID NO:1. For example, an amino acid sequence of a Semaphorin 3B polypeptide can have at least 80% sequence identity (e.g., about 82% sequence identity, about 85% sequence identity, about 88% sequence identity, about 90% sequence identity, about 93% sequence identity, about 95% sequence identity, about 97% sequence identity, about 98% sequence identity, or about 99% sequence identity) to the amino acid sequence set forth in SEQ ID NO:1. Percent sequence identity is calculated by determining the number of matched positions in aligned amino acid sequences, dividing the number of matched positions by the total number of aligned amino acids, respectively, and multiplying by 100. A matched position refers to a position in which identical amino acid occur at the same position in aligned sequences. Sequences can be aligned using the algorithm described by Altschul et al. (*Nucleic Acids Res.*, 25:3389-3402 (1997)) as incorporated into BLAST (basic local alignment search tool) programs, available at ncbi.nlm.nih.gov on the World Wide Web. BLAST searches or alignments can be performed to determine percent sequence identity between an amino acid and any other sequence or portion thereof using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between an amino acid sequence and another sequence, the default parameters of the respective programs can be used. In some cases, a human Semaphorin 3B polypeptide can have the amino acid sequence set forth in FIG. 2B.

Once a mammal (e.g., a human) having membranous nephropathy is identified as having autoantibodies specific for a Semaphorin 3B polypeptide as described herein, the mammal can be classified as having membranous nephropathy that includes the presence of those autoantibodies (e.g., membranous nephropathy that includes the presence of anti-Semaphorin 3B autoantibodies). In some cases, a mammal (e.g., a human) having membranous nephropathy that is identified as having autoantibodies specific for a Semaphorin 3B polypeptide as described herein can be classified as having membranous nephropathy that includes kidney tissue having an elevated level of Semaphorin 3B polypeptides.

Once a mammal (e.g., a human) having membranous nephropathy is identified as having kidney tissue (e.g., GBM) having an elevated level of a Semaphorin 3B polypeptide as described herein, the mammal can be classified as having membranous nephropathy that includes the presence of that kidney tissue (e.g., membranous nephropathy that includes the presence of kidney tissue such as GBM having an elevated level of Semaphorin 3B polypeptides). In some cases, a mammal (e.g., a human) having membranous nephropathy that is identified as having kidney tissue (e.g., GBM) having an elevated level of a Semaphorin 3B polypeptide as described herein can be classified as having membranous nephropathy that includes autoantibodies specific for a Semaphorin 3B polypeptide.

As described herein, this document also provides methods and materials for treating a mammal having membranous nephropathy. For example, a mammal (e.g., a human) having membranous nephropathy that is identified as having (a) autoantibodies specific for a Semaphorin 3B polypeptide and/or (b) kidney tissue (e.g., GBM) having an elevated level of a Semaphorin 3B polypeptide as described herein can be treated with one or more immunosuppressants. In some cases, a mammal (e.g., a human) having membranous nephropathy that is identified as having (a) autoantibodies specific for a Semaphorin 3B polypeptide and/or (b) kidney tissue (e.g., GBM) having an elevated level of a Semaphorin 3B polypeptide as described herein can be administered, or instructed to self-administer, one or more immunosuppressants to treat membranous nephropathy.

In some cases, a mammal (e.g., a human) having membranous nephropathy can be administered one or more immunosuppressants (e.g., anti-CD20 antibodies such as rituximab) to treat membranous nephropathy without attempting to determine if the mammal has autoantibodies specific for the following six polypeptides: a Semaphorin 3B polypeptide, a NELL-1 polypeptide, an EXT1 polypeptide, an EXT2 polypeptide, a PLA2R polypeptide, and a THSD7A polypeptide. In some cases, a mammal (e.g., a human) having membranous nephropathy can be administered one or more immunosuppressants (e.g., anti-CD20 antibodies such as rituximab) to treat membranous nephropathy without attempting to determine if the mammal has kidney tissue (e.g., GBM) having an elevated level of any of the following six polypeptides: a Semaphorin 3B polypeptide, a NELL-1 polypeptide, an EXT1 polypeptide, an EXT2 polypeptide, a PLA2R polypeptide, and a THSD7A polypeptide. In some cases, a mammal (e.g., a human) having membranous nephropathy can be administered one or more immunosuppressants (e.g., anti-CD20 antibodies such as rituximab) to treat membranous nephropathy without attempting to determine if the mammal has autoantibodies specific for those six polypeptides and without attempting to determine if the mammal has kidney tissue (e.g., GBM) having an elevated level of any of those six polypeptides. In some cases, a mammal (e.g., a human) having membranous nephropathy that is administered one or more immunosuppressants (e.g., anti-CD20 antibodies such as rituximab) to treat membranous nephropathy without attempting to determine the presence of such autoantibodies and such kidney tissue (e.g., GBM) can have autoantibodies specific for a Semaphorin 3B polypeptide, can have autoantibodies specific for a NELL-1 polypeptide, can have autoantibodies specific for an EXT1 polypeptide, can have autoantibodies specific for an EXT2 polypeptide, can have autoantibodies specific for a PLA2R polypeptide, or can have autoantibodies specific for a THSD7A polypeptide.

Any appropriate immunosuppressant can be administered to a mammal (e.g., a human that was identified as having (a) autoantibodies specific for a Semaphorin 3B polypeptide and/or (b) kidney tissue (e.g., GBM) having an elevated level of a Semaphorin 3B polypeptide as described herein) to treat membranous nephropathy. In some cases, an immunosuppressant used as described herein to treat membranous nephropathy can reduce inflammation and/or reduce B-cell autoantibody production within a mammal. Examples of immunosuppressants that can be used as described herein to treat membranous nephropathy include, without limitation, mycophenolate mofetil (e.g., Cellcept); steroids such as prednisone; B-cell inhibitors such as anti-CD20 antibodies (e.g., rituximab); calcineurin inhibitors such as cyclosporine and tacrolimus; and alkylating agents/chemotherapeutic drugs such as cyclophosphamide.

In some cases, two or more (e.g., two, three, four, five, six, or more) immunosuppressants can be administered to a mammal having membranous nephropathy (e.g., a human that was identified as having (a) autoantibodies specific for a Semaphorin 3B polypeptide and/or (b) kidney tissue (e.g., GBM) having an elevated level of a Semaphorin 3B polypeptide as described herein). For example, two immunosuppressants (e.g., prednisone and Cellcept) can be administered to a human having membranous nephropathy.

In some cases, one or more immunosuppressants can be administered to a mammal once or multiple times over a period of time ranging from days to months. In some cases, one or more immunosuppressive drugs can be given to achieve remission of membranous nephropathy, and then given during follow up periods to prevent relapse of the membranous nephropathy. In some cases, one or more immunosuppressants can be formulated into a pharmaceutically acceptable composition for administration to a mammal (e.g., a human) having membranous nephropathy to reduce inflammation and/or to reduce B-cell autoantibody production within that mammal. For example, a therapeutically effective amount of an immunosuppressant can be formulated together with one or more pharmaceutically acceptable carriers (additives) and/or diluents. A pharmaceutical composition can be formulated for administration in solid or liquid form including, without limitation, in the form of sterile solutions, suspensions, sustained-release formulations, tablets, capsules, pills, powders, or granules.

Pharmaceutically acceptable carriers, fillers, and vehicles that can be used in a pharmaceutical composition described herein can include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

A pharmaceutical composition containing one or more immunosuppressants can be designed for oral or parenteral (including subcutaneous, intramuscular, intravenous, and intradermal) administration. When being administered orally, a pharmaceutical composition can be in the form of a pill, tablet, or capsule. Compositions suitable for parenteral administration can include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and can be stored in a freeze dried (lyophilized) condition requiring the addition of the sterile liquid carrier, for example, water for injections, immediately prior to use. Extemporaneous injection solutions and suspensions can be prepared from sterile powders, granules, and tablets.

In some cases, a pharmaceutically acceptable composition including one or more immunosuppressants can be administered locally or systemically. For example, a composition provided herein can be administered locally by intravenous injection or blood infusion. In some cases, a composition provided herein can be administered systemically, orally, or by injection to a mammal (e.g., a human).

Effective doses can vary depending on the severity of the nephropathy, the route of administration, the age and general health condition of the subject, excipient usage, the possibility of co-usage with other therapeutic treatments, and the judgment of the treating physician.

An effective amount of a composition containing one or more immunosuppressants can be any amount that reduces inflammation or B-cell autoantibody production (e.g., B-cell antibody production inhibition or reduction in the number of B-cells) within a mammal having membranous nephropathy without producing significant toxicity to the mammal. For example, an effective amount of rituximab to treat membranous nephropathy as described herein can be from about 500 mg to about 1.5 g (e.g., from about 500 mg to about 1.25 g, from about 500 mg to about 1.0 g, from about 500 mg to about 750 mg, from about 750 mg to about 1.5 g, from about 1 g to about 1.5 g, or from about 1.25 g to about 1.5 g) administered IV about two weeks apart. In some cases, an effective amount of rituximab to treat membranous nephropathy as described herein can be from about 200 mg/m$^2$ to about 500 mg/m$^2$ (e.g., from about 200 mg/m$^2$ to about 450 mg/m$^2$, from about 200 mg/m$^2$ to about 400 mg/m$^2$, from about 200 mg/m$^2$ to about 375 mg/m$^2$, from about 250 mg/m$^2$ to about 500 mg/m$^2$, from about 300 mg/m$^2$ to about 500 mg/m$^2$, from about 350 mg/m$^2$ to about 500 mg/m$^2$, or from about 350 mg/m$^2$ to about 400 mg/m$^2$) administered weekly for about four weeks. If a particular mammal fails to respond to a particular amount, then the amount of an immunosuppressant can be increased by, for example, two fold. After receiving this higher amount, the mammal can be monitored for both responsiveness to the treatment and toxicity symptoms, and adjustments made accordingly. For example, levels of anti-Semaphorin 3B autoantibodies present within the mammal (e.g., within the blood of the mammal) can be monitored by an appropriate method (e.g., ELISA). In some cases, the effective amount of a composition containing one or more immunosuppressants can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition can require an increase or decrease in the actual effective amount administered.

The frequency of administration of one or more immunosuppressants can be any amount that reduces inflammation or B-cell autoantibody production (e.g., B-cell antibody production inhibition or reduction in the number of B-cells) within a mammal having membranous nephropathy without producing significant toxicity to the mammal. For example, the frequency of administration of an immunosuppressant can be from about once a day to about once a month (e.g., from about once a week to about once every other week). The frequency of administration of one or more immunosuppressants can remain constant or can be variable during the duration of treatment. A course of treatment with a composition containing one or more immunosuppressants can include rest periods. For example, a composition containing one or more immunosuppressants can be administered daily over a two-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition may require an increase or decrease in administration frequency.

An effective duration for administering a composition containing one or more immunosuppressants can be any duration that reduces inflammation or B-cell autoantibody production (e.g., B-cell antibody production inhibition or reduction in the number of B-cells) within a mammal having membranous nephropathy without producing significant toxicity to the mammal. In some cases, the effective duration can vary from several days to several months. In general, the effective duration for administering a composition containing one or more immunosuppressants to treat membranous nephropathy can range in duration from about one month to about five years (e.g., from about two months to about five years, from about three months to about five years, from about six months to about five years, from about eight months to about five years, from about one year to about five years, from about one month to about four years, from about one month to about three years, from about one month to about two years, from about six months to about four years, from about six months to about three years, or from about six months to about two years). In some cases, the effective duration for administering a composition containing one or more immunosuppressants to treat membranous nephropathy can be for as long as the mammal is alive. Multiple factors can influence the actual effective duration used for a particular treatment. For example, an effective duration can vary with the frequency of administration, effective amount, use of multiple treatment agents, route of administration, and severity of the condition being treated.

In some cases, a course of treatment and/or the severity of one or more symptoms related to membranous nephropathy can be monitored. Any appropriate method can be used to determine whether or not membranous nephropathy is being treated. For example, immunological techniques (e.g., ELISA) can be performed to determine if the level of autoantibodies (e.g., anti-Semaphorin 3B autoantibodies, anti-NELL-1 autoantibodies, anti-EXT1 autoantibodies, anti-EXT2 autoantibodies, anti-PLA2R autoantibodies, and/ or anti-THSD7A autoantibodies) present within a mammal being treated as described herein is reduced following the administration of one or more immunosuppressants. Remission and relapse of the disease can be monitored by testing for one or more markers for membranous nephropathy. In some cases, remission can be ascertained by detecting the disappearance or reduction of autoantibodies to Semaphorin 3B, NELL-1, THSD7A, PLA2R, EXT1, and/or EXT2 in the sera. In some cases, relapse of membranous nephropathy can be ascertained by a reappearance or elevation of autoantibodies to Semaphorin 3B, NELL-1, THSD7A, PLA2R, EXT1, and/or EXT2 in the sera.

The invention will be further described in the following examples, which do not limit the scope of the invention described in the claims.

EXAMPLES

Example 1—Semaphorin 3B-Associated Membranous Nephropathy

The results provided herein demonstrate that Semaphorin 3B polypeptides are present in a subset of PLA2R-, THSD7A-, EXT1-, EXT2-, and NELL1-negative MN patients representing distinct type of primary MN. Accordingly, the presence of Semaphorin 3B polypeptides in a sample obtained from a patient (e.g., a human) can be used to identify the mammal as having Semaphorin 3B positive MN.

Mayo Clinic Cohort

Tandem mass spectrometry (MS/MS) was performed in selected kidney biopsies of 70 cases of PLA2R-negative MN received at the Mayo Clinic for analysis, and the unique protein, Semaphorin 3B (Sema3B), was detected in two cases. The 70 cases included both primary and secondary membranous nephritis. Immunohistochemistry (IHC) was then performed to confirm the MS/MS results. In addition, 160 PLA2R-negative MN (including the 68 negative and 2 positive on MS/MS) were screened by IHC for Sema3B. Only one more positive case was detected. Other than four pediatric cases (<18 years of age), the remaining cases were all adult cases.

French and Italian Validation Cohort

A total of 118 biopsies were stained for Sema3B, of which 59 were from the French adult cohort, 43 from the Italian pediatric cohort, and 16 from the French pediatric cohort. All cases were PLA2R-, THSD7A-, EXT1-, EXT2-, and NELL1-negative MN. Each pediatric cohort included 9 lupus class V cases.

Control Cases

For control cases, MS/MS was performed on 111 cases that included 15 cases of time 0 transplant biopsies, 17 cases of minimal change disease, 44 cases of focal segmental glomerulosclerosis, 7 cases of diabetic glomerulosclerosis, 5 cases of IgA nephropathy, and 23 cases of PLA2R-positive membranous nephropathy. For control IHC, 45 cases including the following were used: 9 cases of minimal change disease, 9 cases of focal segmental glomerulosclerosis, 4 cases of IgA nephropathy, 7 cases of diabetes, 15 cases of PLA2R-positive MN, and 1 case of time 0 transplant protocol biopsy.

These biopsies were received in the Renal Pathology Laboratory, Department of Laboratory Medicine and Pathology, Mayo Clinic, for diagnosis and interpretation. Light microscopy, immunofluorescence microscopy including PLA2R studies, and electron microscopy were performed in each case of MN. The clinical information was obtained from the accompanying charts.

Laser Microdissection and Mass Spectrometry

Protein identification by laser capture microdissection, trypsin digestion, nano-LC orbitrap tandem mass spectrometry (MS/MS):

For each case 10 micron thick formalin-fixed paraffin sections (FFPE) were obtained and mounted on a special PEN membrane laser microdissection slide. Using a Zeiss Palm Microbean microscope, the glomeruli were microdissected to reach approximately 250,000 to 500,000 $\mu m^2$ per case. Resulting FFPE fragments were digested with trypsin and collected for MS/MS analysis. The trypsin digested peptides were identified by nano-flow liquid chromatography electrospray tandem MS/MS (nanoLC-ESI-MS/MS) using a Thermo Scientific Q-Exactive Mass Spectrometer (Thermo Fisher Scientific, Bremen, Germany) coupled to a Thermo Ultimate 3000 RSLCnano HPLC system. All MS/MS samples were analyzed using Mascot and X! Tandem set up to search a Swissprot human database. Scaffold (version 4.8.3, Proteome Software Inc., Portland, OR) was used to validate MS/MS based peptide and protein identifications. Peptide identifications were accepted at greater than 95.0% probability by the Scaffold Local FDR algorithm with protein identifications requiring a two peptide minimum and a 95% probability using Protein Prophet.14

Immunohistochemical Staining for Semaphorin 3B

Tissue sectioning and IHC staining were performed at the Pathology Research Core (Mayo Clinic, Rochester, MN) using the Leica Bond RX stainer (Leica). FFPE tissues were sectioned at 5 microns, and IHC staining was performed on-line. Slides for Semaphorin 3B stain were retrieved for 20 minutes using Epitope Retrieval 1 (Citrate; Leica) and incubated in Protein Block (Dako) for 5 minutes. The Semaphorin 3B primary antibody (Rb. Polyclonal; Abcam #ab48197) was diluted to 1:200 in Background Reducing Diluent (Dako) and incubated for 15 minutes. The detection system used was Polymer Refine Detection System (Leica). This system included the hydrogen peroxidase block, post primary and polymer reagent, DAB, and Hematoxylin. Immunostaining visualization was achieved by incubating slides 10 minutes in DAB and DAB buffer (1:19 mixture) from the Bond Polymer Refine Detection System. To this point, slides were rinsed between steps with 1× Bond Wash Buffer (Leica). Slides were counterstained for five minutes using Schmidt hematoxylin and molecular biology grade water (1:1 mixture), followed by several rinses in 1× Bond wash buffer and distilled water, which was not the hematoxylin provided with the Refine kit. Once the immunochemistry process was completed, slides were removed from the stainer and rinsed in tap water for five minutes. Slides were dehydrated in increasing concentrations of ethyl alcohol and cleared in 3 changes of xylene prior to permanent cover slipping in xylene-based medium.

Immunofluorescence Staining for Sema 3B and Co-Localization Analysis

Immunofluorescence staining was performed on FFPE sections retrieved for 30 minutes using target retrieval solution high pH (Dako) in pressure cooker equipment (BioSB). The Sema 3B primary antibody (rabbit polyclonal, Abcam antibodies) was diluted to 1:100 in blocking solution (2% calf fetal serum and 2% normal goat serum) and incubated overnight at 4° C. with retrieved biopsy sections. Next, the slides were incubated with secondary antibody the goat Alexa488-conjugated anti-rabbit Fab IgG antibodies (Life technologies). Next, anti-human IgG Alexa Fluor 647 rabbit monoclonal antibody (Sigma) was reacted with the retrieved tissue following the staining for Sema 3B as described above. Finally, slides were mounted in mounted medium (Thermo Scientific) and covered with LDS2460EP cover slips. Co-localization of Sema3B and IgG along the glomerular basement membranes was examined by confocal microscopy using a Leica TCS-SP2 and analyzed with Leica Confocal Software version 2.61, Wetzlar, Germany.

Western Blot Analysis

10 μg of Sema3B overexpression lysate (OriGene) was diluted with non-reducing Laemmli sample buffer (Bio-Rad) and boiled for 10 minutes. Samples were loaded into Criterion 4-15% TGX gels (Bio-Rad) and electrophoresed in Tris-glycine-SDS running buffer. Proteins were transferred to poly vinylidene difluoride membranes according to standard protocols, and then membranes were blocked with Pierce Protein-Free Blocking buffer (Thermo Scientific). Membranes were incubated overnight at 4° C. with sera from patients, controls (dilution 1:50), and rabbit polyclonal antibodies (dilution 1:2000) against Sema3B (Abcam). Subsequently, blots were washed and incubated for 2 hours at room temperature with goat-anti human or goat anti-rabbit IgG, AP conjugate (Sigma). Immunoreactive proteins were visualized with BCIP/NBT liquid substrate system (Sigma).

Results

Discovery Cohort

Figure 1:
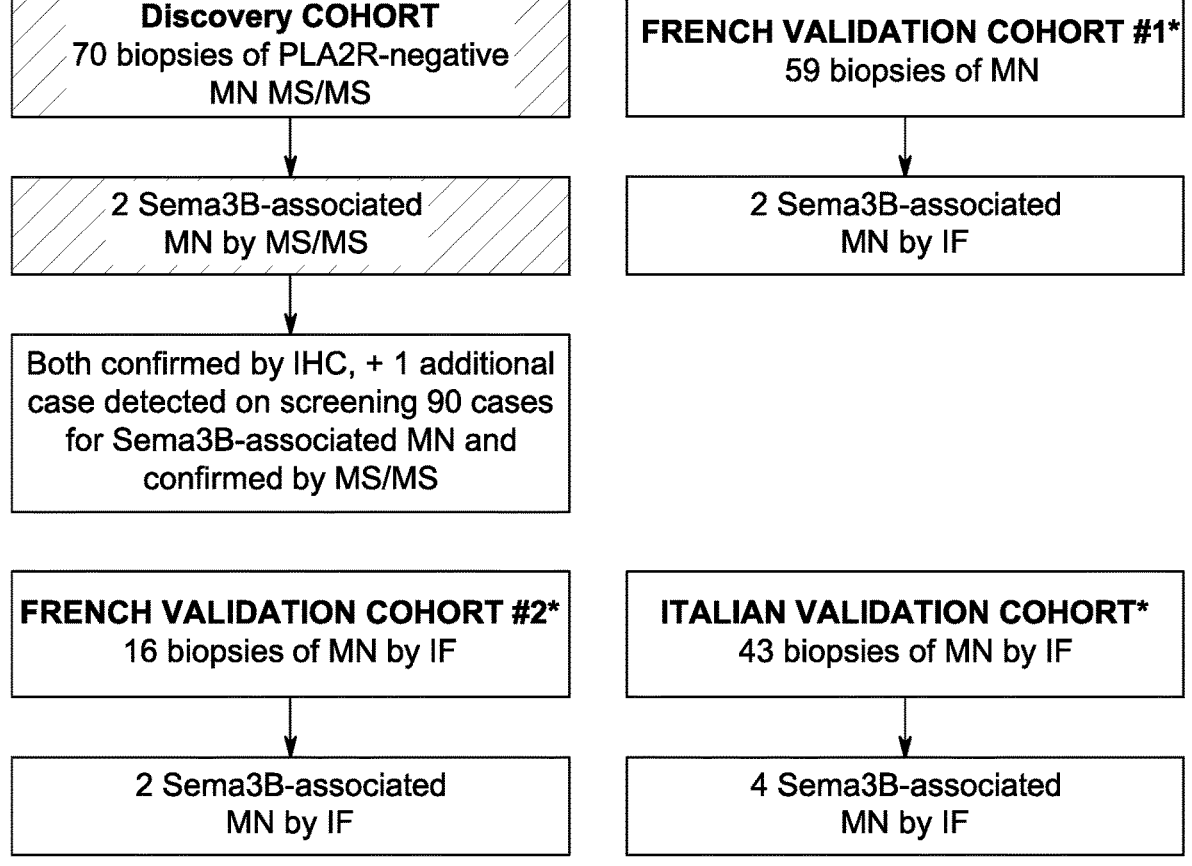
FIG. 1. Flowchart of the discovery and validation cohorts. Initial studies were done by mass spectrometry (MS) studies using 70 PLA2R negative MN. Semaphorin 3B (Sema3B) was detected in 2 cases which was then confirmed by immunohistochemistry (IHC). All 70 cases were negative for NELL-1 and EXT1/EXT2 by MS. An additional number (n=90) of PLA2R negative MN were then examined for Sema3B, which yielded one positive Sema3B MN case. Three validation cohorts were studied. The first (French) validation cohort included 59 cases, the second (French) cohort included 16 pediatric cases, and the Italian cohort that included 43 pediatric cases. * All cases were negative for PLA2R, THSD7A, NELL-1, and EXT1/EXT2 staining by IF. Top two boxes on the left indicate detection and confirmation of Sema3B by MS, remaining boxes indicate detection by IHC/IF.

Laser Dissection and Mass Spectrometry (MS/MS) Detection of Semaphorin 3B in PLA2R-Negative MN Biopsies A unique protein, Semaphorin 3B (Sema3B), was detected by MS/MS in the glomeruli of three cases (patients 1-3) of MN (FIG. 1). The counts ranged from 10 to 42 with an average total spectral count of 23.7 (SD±16.5). The average spectral counts of Sema3B were lower than PLA2R (86.1, S.D±27.5), NELL-1 (63.1, S.D±21.6), and EXT1/EXT2 (EXT1 65.3, S.D±34.6, EXT2 83.4, S.D±38.4) in PLA2R-, NELL-1-, and EXT1/EXT2-associated MN, respectively (Sethi et al., *Kidney International*, 97:163-174 (2020); and Sethi et al., *J. Am. Soc. Nephrol.*, 30:1123-1136 (2019)). However, the presence of Sema3B was unique in this subset of MN, and all control cases including PLA2R-positive cases were negative for Sema3B. The spectral counts of Sema3B in the three cases, along with representative sequence coverage map of Sema3B is shown in FIG. 2. The MS/MS spectra match from one case are shown in FIG. 3. None of the cases showed any spectral counts for THSD7A.

All four classes of Ig were detected in Sema3B associated MN, with average spectral counts of IgG1 25.0 (S.D±4.0), IgG2 22.7 (S.D±4.5), IgG3 25.0 (S.D±9.5), and IgG4 17.0 (S.D±5.3).

Immunohistochemical (IHC) Staining for Sema3B in PLA2R-Negative MN Biopsies

IHC staining was performed for Sema3B in all three cases positive on MS/MS studies. All cases showed positive (2-3+/3) granular staining for Sema3B along the GBM. There was no significant mesangial staining (FIG. 4A). There was no staining along the Bowman's capsule, tubular basement membranes, or in vessel walls. The positive Sema3B granular staining mirrored the granular IgG along the GBM seen in each case. All control cases were negative for Sema3B. Representative negative staining for Sema3B in PLA2R-associated MN, FSGS, IgA nephropathy, and diabetes is shown in FIG. 4B.

Validation Cohorts

Given the results obtained in the Mayo cohort showing one pediatric case (#3), three validation cohorts (one adult (French cohort 1) and 2 pediatric (Italian cohort, French cohort 2) cohorts) were analyzed (FIG. 1).

Sema3B was detected using immunofluorescence microscopy (IF) studies on paraffin sections after antigen retrieval. Patient 4 of the validation cohort had both IHC and IF studies performed.

French Cohort 1

Two adult cases (patients 4 and 5) out of 59 PLA2R-, THSD7A-, EXT1/EXT2-, and NELL-1-negative primary MN were positive for Sema3B. One case (patient 4) was detected by IHC and was then confirmed by IF studies on paraffin sections (FIGS. 5A and 5B). Patient 5 had three biopsies performed at the age of one, 6, and 19 years, showing granular staining for Sema3B along the GBM (Biopsy at age one and 19 shown in FIGS. 5C, 5D, and 6). Thus, Sema3B-associated MN appeared enriched in pediatric patients. Given this finding, Sema3B was screened for in a larger cohort of membranous nephropathy in the pediatric age group (Italian cohort and French cohort #2).

Italian Cohort

Four cases (patients 6, 7, 8, and 9) out of 43 pediatric cases negative for PLA2R-, THSD7A-, EXT1/EXT2-, and NELL-1 exhibited bright granular staining for Sema3B along the GBM (FIGS. 5E, 5F, and 5G). Of the 43 cases, six had lupus class V MN, and three had Class II or III+V. All nine of these were negative for Sema3B.

French Cohort 2

An additional two cases (patients 9 and 10) out of 16 pediatric cases negative for PLA2R-, THSD7A-, EXT1/EXT2-, and NELL-1 exhibited the bright granular deposits of Sema3B along the GBM (FIGS. 5H and 5I). Of the 16 cases, nine had lupus class V MN, and these nine cases were negative for Sema3B.

The granular GBM staining and absence of mesangial or Bowman capsule staining in all cases was noted (FIGS. 5A-J).

Confocal Microscopy

Figure 8:
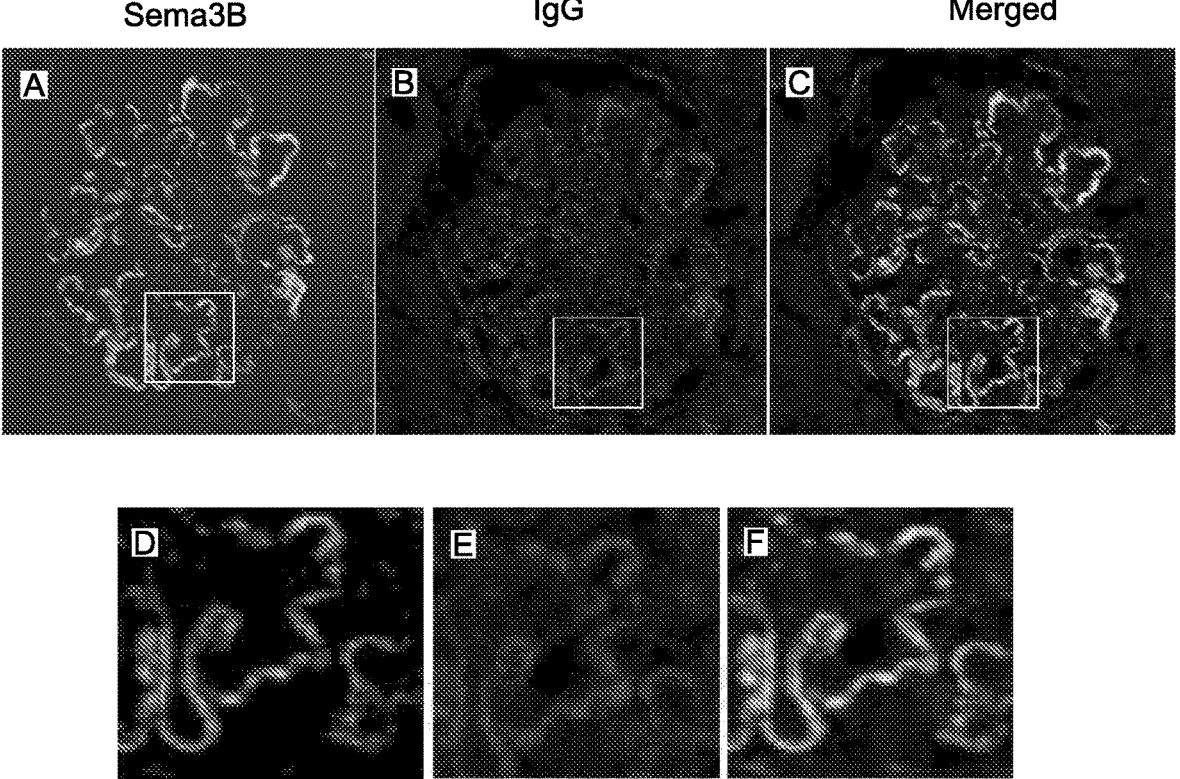

Confocal immunofluorescence microscopy was performed to determine whether Sema3B and IgG co-localize along the GBM (FIGS. 7A-E). Bright granular staining for Sema3B (green) and IgG (red) was seen along the GBM (FIGS. 7A and 7B). Furthermore, superimposition of the two signals showed co-localization resulting in a yellow signal (FIG. 7C). Laser quantitative analysis (FIGS. 7D and 7E) also confirmed the co-localization of Sema3B and IgG further corroborating that the subepithelial deposits contain both Sema3B and IgG. A second case also was evaluated (FIG. 8).

Western Blot Analysis

Western blot analyses were performed using Sema3B over expression lysates to determine the presence of circulating anti-Sema3B autoantibodies in the serum of four patients (patient 3, 4, 5, and 8) (FIG. 9). Three of the four patients exhibited reactivity against Sema3B under non-reducing conditions (patients were labeled as MN in the table). A band was seen at around 55 kDa representing the secreted form of the protein. Sera from patients with PLA2R-associated MN did not exhibit any reactivity against Sema3B. The last serum (MN5) was a sample after a long-term immunosuppressive treatment.

Clinical and Kidney Biopsy Findings of Sema3B Associated MN 11 cases of Sema3B-associated MN were identified: three from the Mayo Clinic cohort, two from the French validation cohort #1, four from the Italian validation cohort, and two from the French validation cohort #2 (Table 1). There were seven males and four females. Of the 11 cases, eight (73%) were pediatric patients (<18 years of age), and three (27%) were adult patients. Of the Mayo Clinic cohort (patients 1-3), one was a pediatric patient (1 out 4 pediatric PLA2R-negative MN cases tested for Sema3B, 25%) and two patients were adults (two out of 160 primary and secondary PLA2R-negative MN tested, 1.25%; secondary PLA2R-negative cases included class V membranous lupus nephritis). Of the validation cohorts (French adult cohort, Italian pediatric cohort, and French pediatric cohort), there were eight pediatric patients (of 60 PLA2R-negative pediatric MN tested including case 5, 13.3%) and one adult patient (one out of 58 PLA2R-negative adult MN tested excluding case 5, 1.7%). In patient 5, MN was diagnosed at the age of 1 year (biopsy performed because of steroid-resistant NS) and repeat biopsy performed six and 18 years later revealed grade II MN. Each of the pediatric cohorts included nine patients with lupus MN class V. In total, 6/41 (14.6%) non-lupus pediatric cases tested were Sema3B positive.

TABLE 1

| | | | | | Clinical and pathologic findings in Sema3B-associated MN | | | | |
|---|---|---|---|---|---|---|---|---|---|
| Case | Age/Sex | Urinary protein gms/24 hour | Serum Cr (mg/dL) | S. Cr/ Urinary protein/24 hour (FU months) | Sclerosed/ total glomeruli | IFTA | IF | EM | TBM |
| 1 | 41/F | 7.9 | 0.74 | 0.6/no proteinuria (16 months) | 1/22 | 0 | IgG 3+ (IgG1) C3 2+ | I-II | No |
| 2 | 28/F | 6.2 | 0.4 | 0.43/400 mg (18 months) | 1/36 | 0 | IgG 3+ (IgG4) C3 2+ | I-II | No |
| 3 | 2/M (MN3) | 5 | 0.5 | 0.35/150 mg (24 months) | 0/60 | 10 | IgG 3+ (IgG4) C3 3+ | I-II | Yes |
| 4 | 40/F (MN4) | 17.3 | 0.9 | 0.6/no proteinuria (10 years) | 0/19 | 0 | IgG 1+ C3 1+ C1q 1+ | Not done | Not done |
| 5 | 19/M** (onset 1 year) | 0.4 | 0.7 | 0.9/400 mg (18 years) | 0/6 | 0 | IgG 3+ (IgG1) C3 2+ | II | Yes |
| 6 | 1 year and 9 month/F | UP/CR ratio 6.81, Micro-hematuria++ | 0.21 | UP/CR ratio 0.23 | 0/20 | 0 | IgG 3+ C3 2+ C1q 1+ | III | Yes |
| 7 | 17/M | UP/CR ratio 0.78 | 0.6 | UP/CR ratio 0.1 (absent) | 1/30 | 0 | IgG 3+ C1q 2+ C3 3+ | II | No |

TABLE 1-continued

Clinical and pathologic findings in Sema3B-associated MN

| Case | Age/Sex | Urinary protein gms/24 hour | Serum Cr (mg/dL) | S. Cr/ Urinary protein/24 hour (FU months) | Sclerosed/ total glomeruli | IFTA | IF | EM | TBM |
|------|---------|------|------|------|------|------|------|------|------|
| 8 | 9/M (onset 2 years) | UP/CR ratio 0.94 | 0.45 | UP/CR ratio 0.09 (absent) | 3/16 | 30 | IgG 3+ C3 2+ | II | No |
| 9 | 2/M | UP/CR ratio 1.95 | 0.13 | UP/CR ratio 0.12 (absent) | 1/18 | 0 | IgG 3+ IgM 1+ C3+ | II | Yes |
| 10 | 14/M | 3 | 0.64 | NA | 0/9 | 0 | IgG 3+ IgA 2+, C1q 1+ C3 3+ | II | No |
| 11 | 16/M | 12 | 0.83 | Dialysis | 0/9 | 5 | IgG 3+ IgM 3+ C1q2+ | Not done | Not done |

*MN was diagnosed at the age of 1 year (biopsy performed because of steroid-resistant NS), repeat biopsy six and 18 years later;
IFTA = interstitial fibrosis and tubular atrophy; IF = immunofluorescence microscopy; EM = electron microscopy; TBM = tubular
basement membrane deposits; FU = follow up; UP/CR = urinary protein/urinary creatinine ratio; and NA = not available.

The average age of the pediatric patients at disease onset was 6.9 years (S.D±6.8), and the average age of the three adult patients was 36.3 (S.D±7.2). Two children had extra-renal features of auto-immunity (type 1 diabetes in patient 10, and idiopathic thrombocytopenic purpura with positive ANA in patient 11). The average serum creatinine was 0.5 mg/dL (S.D±0.2), and 24-hour urinary protein was 7.4 grams (n=7, S.D±5.7).

Figure 6:
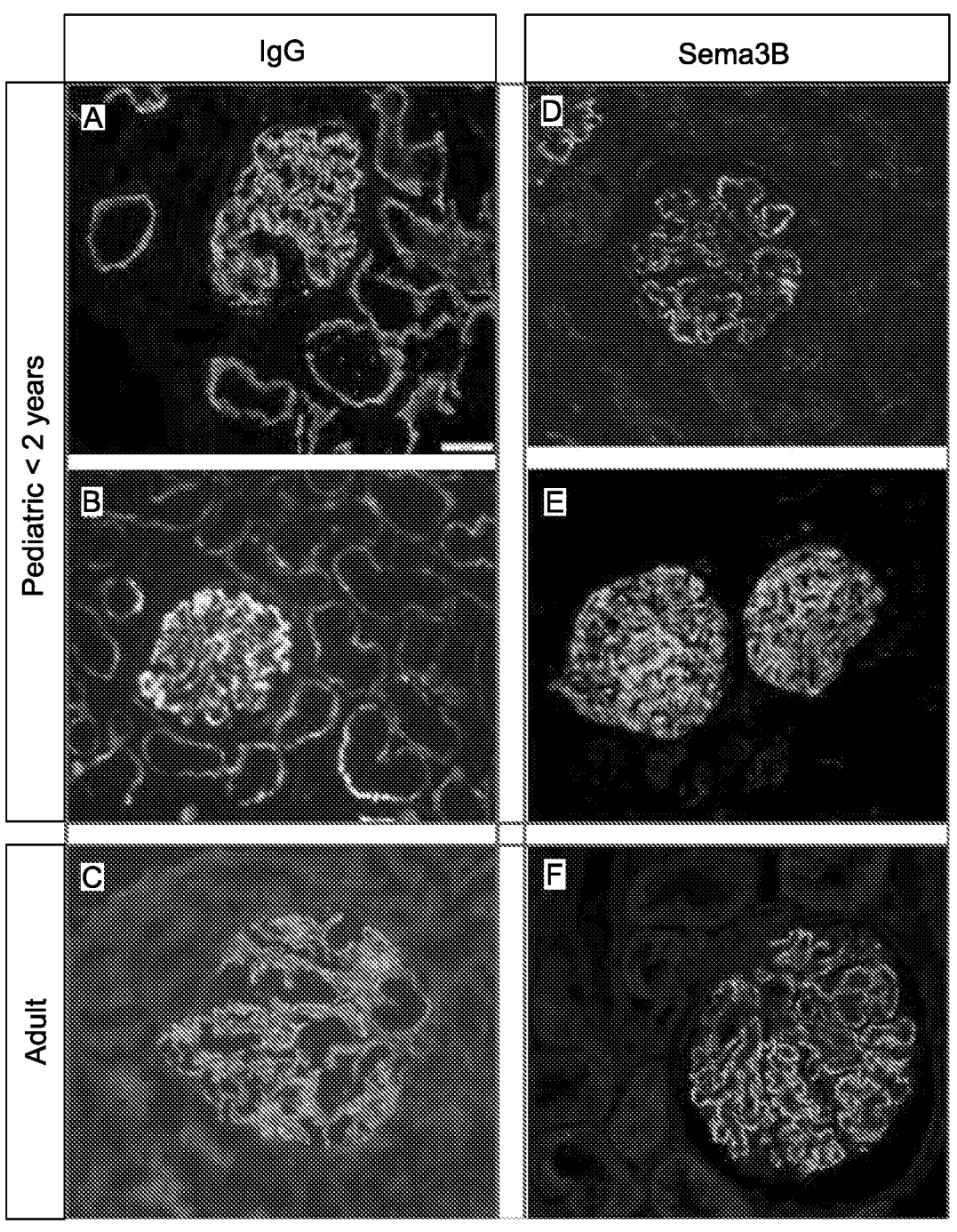
Figure 10:
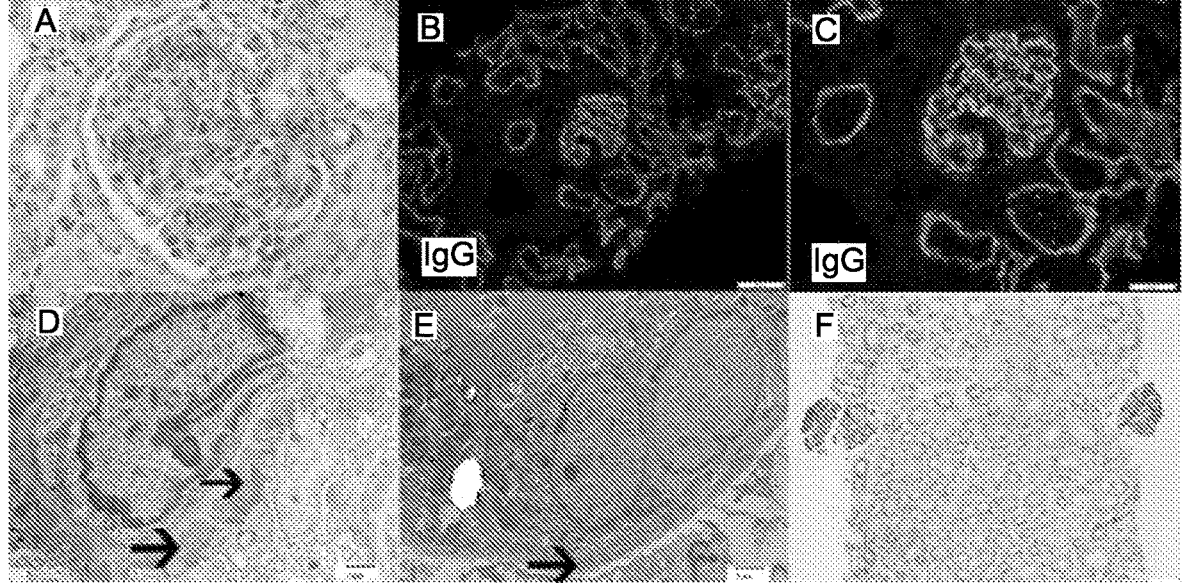

Kidney biopsy in all cases revealed features of MN with thickened glomerular basement membranes. Immunofluorescence microscopy revealed granular IgG and Sema3B deposits along the glomerular capillary walls. Interestingly, four cases (patients 3, 5, 6, and 9, all pediatric, <2 years of age at onset) also exhibited tubular basement membrane staining for IgG in a granular pattern (FIGS. 6 and 10). In patient 5, granular IgG deposits along tubular basement membranes were noted in the first biopsy (one year of age) but disappeared thereafter. However, the tubular basement membrane deposits were negative for Sema3B staining in all biopsies (FIGS. 6D, 6E, and 6F). Electron microscopy was performed in all patients except patients 4, 10, and 11. Of the cases that were graded as stage II, it revealed glomerular subepithelial deposits in most cases. The deposits observed along tubular basement membranes were confirmed or revealed by EM in three cases (patients 3, 6, and 9). Tubuloreticular inclusions were noted in these cases as well.

Treatment and Follow Up

Mayo Clinic cohort: Patient 1 and 2 received only angiotensin converting enzyme inhibitors and went to remission with minimal proteinuria (<500 mg/24 hours) at last follow up of 18 and 24 months, respectively. Patient 3 received steroids, tacrolimus, and angiotensin converting enzyme (ACE) inhibitors and also went into remission. At last follow-up (24-months), the proteinuria was 150 mg/24 hours.

French adult cohort: Patient 4 was treated for 4 months with angiotensin converting enzyme inhibitors. Because of persisting severe nephrotic syndrome, she was given rituximab, two infusions of 375 mg/m² at 2-week interval, followed by a third infusion at 3 months. Thereafter, she reached complete remission, which was maintained after 10 years (daily proteinuria <500 mg, no more detectable anti-Sema3B antibody in serum). Patient 5 was diagnosed at the age of one year. He failed to respond to cyclosporine and from the age of 5 to the age of 7 years, he was treated with mycophenolate mofetil that induced complete remission. Six months after mycophenolate mofetil withdrawal, a relapsed occurred. A second biopsy revealed MN stage 2 with disappearance of granular tubular deposits. Mycophenolate mofetil (500 mg twice daily) was resumed and increased to 1 gram twice daily 10 years later because of reappearance of isolated proteinuria without nephrotic syndrome. The patient was assessed at age 19 to consider immunosuppressant withdrawal. Because of persisting low level of proteinuria (400 mg/day) with normal renal function (serum creatinine, 0.9 mg/dL), a third kidney biopsy was performed. The biopsy revealed MN stage 2 with abundant deposits by IF (IgG1, C3, Sema3B) and EM (non-organized electron dense deposits) (FIG. 10). Search for serum anti-Sema3B autoantibodies was negative. Mycophenolate mofetil was then tapered. One year later, the patient was still in complete remission. Anti-Sema3B autoantibodies were not detected.

Italian pediatric cohort: Patient 6 (onset <2 years of age with nephrotic-range proteinuria) was biopsied at disease onset and received oral prednisone tapered in 6 months and cyclosporine A. This led to a complete remission, with a follow-up of 13 months. Patient 7 (onset at age 17 years with proteinuria 16 g/day) received oral prednisone. Due to partial response after two months, a renal biopsy was performed, which revealed a classic MN. He was treated with cyclosporine and an ACE-inhibitor. Prednisone was tapered in four months. The patient responded completely, with a follow-up of 19 months. Patient 8 (age at onset 2 years), who exhibited on the first biopsy a full-house IF (IgG3+, IgM 2+, IgA 3+, C3 2+, C1q 3+ and presented with nephrotic-range proteinuria, normal renal function, negative ANA, no other symptoms), was initially treated with intravenous cyclophosphamide and methylprednisolone bolus followed by maintenance low-dose prednisone and azathioprine. Treatment was tapered and discontinued after about 2 years. The child experienced a first relapse (UP/CR ratio ≥1) 2 years later, revealing on the renal biopsy classic MN, responsive to cyclosporine and again at 9 years of age a relapse that led to a renal biopsy (the one examined herein) confirming classic MN. He was treated with intravenous rituximab with relapse upon tapering of cyclosporine despite repeated doses, and therefore was shifted to tacrolimus with full response. At last follow-up (14 years from onset), he was in remission with normal renal function on low-dose tacrolimus and an ACE-inhibitor. Patients 7 and 8 were siblings.

Patient 9 presented with nephrotic-range proteinuria (UP/CR ratio 16.75) at 2 years of age and was treated with oral prednisone but did not respond fully at four weeks of treatment. Therefore, a renal biopsy was performed showing MN. The patient responded completely to cyclosporine and oral prednisone that was tapered in six months. However, each time cyclosporine was tapered, proteinuria reappeared, and at the age of 7 years, he was treated with rituximab. At last follow-up (5 years from onset), he was in complete remission.

French pediatric cohort: Patient 10 was lost to follow-up. Patient 11 evolved to end stage kidney disease within 3 years, being unresponsive to rituximab, mycophenolate mofetil, and cyclosporine. He suffered from a thromboembolic disease of unknown etiology.

Discussion

MN is the most common cause of nephrotic syndrome in Caucasian adults. It is caused by autoantibodies against target antigen(s) in the GBM. On the other hand, it is a rare cause of nephrotic syndrome in children. In the last decade, groundbreaking research has led to the identification of some of the target MN antigens including PLA2R, THSD7A, NELL-1, and putative antigens EXT1/EXT2 (Tomas et al., *N. Engl. J. Med.*, 371:2277-2287 (2014); Beck et al., *N. Engl. J. Med.*, 361:11-21 (2009); Sethi et al., *Kidney International*, 97:163-174 (2020); and Sethi et al., *J. Am. Soc. Nephrol.*, 30:1123-1136 (2019)).

Yet, these antigens do not account for all cases of MN, and in a significant number of MN, the target antigen is still elusive. As described herein, a combination of laser microdissection, MS/MS, and IHC techniques was used to identify Sema3B from over 1500-2000 proteins detected on MS/MS.

Eight (72.7%) of the 11 Sema3B-associated MN patients were pediatric patients of which five patients developed MN before the age of 2 years. The remaining three patients developed MN at the age of 14, 16, and 17 years. There were only three adult patients detected. The average adult age was 36.3 years, which is still significantly lower than primary MN age group. Thus, Sema3B-associated MN appears primarily to involve pediatric patients or young adults.

In conclusion, Sema3B-associated MN appears to be a unique kidney disease associated with overexpression of Sema3B. Sema3B-associated MN appears to be a distinct type of primary MN that is more likely to be present in pediatric patients, particularly in very young patients with onset <2 years. Sema3B-associated MN should be added to the list of serologically defined MN, including PLA2R-, THSD7A-, and NELL-1-associated MN.

Example 2—Identifying Semaphorin 3B Positive Membranous Nephropathy

A blood sample (e.g., serum) is obtained from a human having membranous nephropathy. The obtained sample is examined for the presence of autoantibodies specific for a Semaphorin 3B polypeptide.

If autoantibodies specific for a Semaphorin 3B polypeptide are detected in the sample, as compared to a control level, then the human classified as having a Semaphorin 3B-positive membranous nephropathy.

Example 3—Treating Semaphorin 3B-Positive Membranous Nephropathy

A human identified as having autoantibodies specific for a Semaphorin 3B polypeptide is administered one or more immunosuppressive agents (e.g., corticosteroids, cyclosporine, or a B-cell reduction or depletion agent such as Rituximab).

The administered immunosuppressive agent(s) can reduce inflammation and/or B-cell autoantibody production.

The administered immunosuppressive agent(s) can reduce the level of autoantibodies specific for a Semaphorin 3B polypeptide present within the human.

Example 4—Identifying Semaphorin 3B-Positive Membranous Nephropathy

A kidney tissue sample is obtained from a human having membranous nephropathy. The obtained sample is examined for an elevated level of a Semaphorin 3B polypeptide.

If an elevated level of a Semaphorin 3B polypeptide is detected in the sample, as compared to a control level, then the human classified as having a Semaphorin 3B-positive membranous nephropathy.

Example 5—Treating Semaphorin 3B-Positive Membranous Nephropathy

A human identified as having an elevated level of a Semaphorin 3B polypeptide is administered one or more immunosuppressive agents (e.g., corticosteroids, cyclosporine, or a B-cell reduction or depletion agent such as Rituximab).

The administered immunosuppressive agent(s) can reduce inflammation and/or B-cell autoantibody production.

The administered immunosuppressive agent(s) can reduce a level of autoantibodies specific for a Semaphorin 3B polypeptide present within the human.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method for treating a mammal having membranous nephropathy, wherein said method comprises:

(a) identifying a mammal as having (i) autoantibodies specific for a polypeptide or (ii) kidney tissue comprising an elevated level of said polypeptide, wherein said polypeptide is a Semaphorin 3B polypeptide, and (b) administering an immunosuppressant to said mammal.

2. The method of claim 1, wherein said mammal is a human.

3. The method of claim 1, wherein said mammal is identified as having said autoantibodies.

4. The method of claim 1, wherein said mammal is identified as having said kidney tissue.

5. The method of claim 1, wherein said immunosuppressant is a B-cell inhibitor.

6. The method of claim 5, wherein said B-cell inhibitor is rituximab.

7. A method for treating a mammal having membranous nephropathy, wherein said method comprises administering an immunosuppressant to a mammal identified as having (i) autoantibodies specific for a polypeptide or (ii) kidney tissue comprising an elevated level of said polypeptide, wherein said polypeptide is a Semaphorin 3B polypeptide.

8. The method of claim 7, wherein said mammal is a human.

9. The method of claim 7, wherein said mammal was identified as having said autoantibodies.

10. The method of claim 7, wherein said mammal was identified as having said kidney tissue.

11. The method of claim 7, wherein said immunosuppressant is a B-cell inhibitor.

12. The method of claim 11, wherein said B-cell inhibitor is rituximab.

\* \* \* \* \*

SEQUENCE LISTING

```
<160> NUMBER OF SEQ ID NOS: 2

<210> SEQ ID NO 1
<211> LENGTH: 749
<212> TYPE: PRT
<213> ORGANISM: Homo sapiens

<400> SEQUENCE: 1
```

```
Met Gly Arg Ala Gly Ala Ala Ala Val Ile Pro Gly Leu Ala Leu Leu
1               5                   10                  15

Trp Ala Val Gly Leu Gly Ser Ala Ala Pro Ser Pro Pro Arg Leu Arg
                20                  25                  30

Leu Ser Phe Gln Glu Leu Gln Ala Trp His Gly Leu Gln Thr Phe Ser
            35                  40                  45

Leu Glu Arg Thr Cys Cys Tyr Gln Ala Leu Leu Val Asp Glu Glu Arg
        50                  55                  60

Gly Arg Leu Phe Val Gly Ala Glu Asn His Val Ala Ser Leu Asn Leu
65                  70                  75                  80

Asp Asn Ile Ser Lys Arg Ala Lys Lys Leu Ala Trp Pro Ala Pro Val
                85                  90                  95

Glu Trp Arg Glu Glu Cys Asn Trp Ala Gly Lys Asp Ile Gly Thr Glu
            100                 105                 110

Cys Met Asn Phe Val Lys Leu Leu His Ala Tyr Asn Arg Thr His Leu
        115                 120                 125

Leu Ala Cys Gly Thr Gly Ala Phe His Pro Thr Cys Ala Phe Val Glu
        130                 135                 140

Val Gly His Arg Ala Glu Glu Pro Val Leu Arg Leu Asp Pro Gly Arg
145                 150                 155                 160

Ile Glu Asp Gly Lys Gly Lys Ser Pro Tyr Asp Pro Arg His Arg Ala
                165                 170                 175

Ala Ser Val Leu Val Gly Glu Glu Leu Tyr Ser Gly Val Ala Ala Asp
            180                 185                 190

Leu Met Gly Arg Asp Phe Thr Ile Phe Arg Ser Leu Gly Gln Arg Pro
        195                 200                 205

Ser Leu Arg Thr Glu Pro His Asp Ser Arg Trp Leu Asn Glu Pro Lys
        210                 215                 220

Phe Val Lys Val Lys Trp Ile Pro Glu Ser Glu Asn Pro Asp Asp Asp
225                 230                 235                 240

Lys Ile Tyr Phe Phe Phe Arg Glu Thr Ala Val Glu Ala Ala Pro Ala
                245                 250                 255

Leu Gly Arg Leu Ser Val Ser Arg Val Gly Gln Ile Cys Arg Asn Asp
            260                 265                 270

Val Gly Gly Gln Arg Ser Leu Val Asn Lys Trp Thr Thr Phe Leu Lys
        275                 280                 285

Ala Arg Leu Val Cys Ser Val Pro Gly Val Glu Gly Asp Thr His Phe
        290                 295                 300

Asp Gln Leu Gln Asp Val Phe Leu Leu Ser Ser Arg Asp His Arg Thr
305                 310                 315                 320

Pro Leu Leu Tyr Ala Val Phe Ser Thr Ser Ser Ser Ile Phe Gln Gly
                325                 330                 335

Ser Ala Val Cys Val Tyr Ser Met Asn Asp Val Arg Arg Ala Phe Leu
            340                 345                 350

Gly Pro Phe Ala His Lys Glu Gly Pro Met His Gln Trp Val Ser Tyr
        355                 360                 365

Gln Gly Arg Val Pro Tyr Pro Arg Pro Gly Met Cys Pro Ser Lys Thr
        370                 375                 380

Phe Gly Thr Phe Ser Ser Thr Lys Asp Phe Pro Asp Asp Val Ile Gln
385                 390                 395                 400

Phe Ala Arg Asn His Pro Leu Met Tyr Asn Ser Val Leu Pro Thr Gly
                405                 410                 415

Gly Arg Pro Leu Phe Leu Gln Val Gly Ala Asn Tyr Thr Phe Thr Gln
```

-continued

```
          420              425               430
Ile Ala Ala Asp Arg Val Ala Ala Ala Asp Gly His Tyr Asp Val Leu
        435              440               445

Phe Ile Gly Thr Asp Val Gly Thr Val Leu Lys Val Ile Ser Val Pro
    450              455              460

Lys Gly Ser Arg Pro Ser Ala Glu Gly Leu Leu Leu Glu Glu Leu His
465              470              475              480

Val Phe Glu Asp Ser Ala Ala Val Thr Ser Met Gln Ile Ser Ser Lys
            485              490              495

Arg His Gln Leu Tyr Val Ala Ser Arg Ser Ala Val Ala Gln Ile Ala
        500              505              510

Leu His Arg Cys Ala Ala His Gly Arg Val Cys Thr Glu Cys Cys Leu
        515              520              525

Ala Arg Asp Pro Tyr Cys Ala Trp Asp Gly Val Ala Cys Thr Arg Phe
        530              535              540

Gln Pro Ser Ala Lys Arg Arg Phe Arg Arg Gln Asp Val Arg Asn Gly
545              550              555              560

Asp Pro Ser Thr Leu Cys Ser Gly Cys Ser Ser Arg Pro Ala Leu Leu
            565              570              575

Glu His Lys Val Phe Gly Val Glu Gly Ser Ser Ala Phe Leu Glu Cys
            580              585              590

Glu Pro Arg Ser Leu Gln Ala Arg Val Glu Trp Thr Phe Gln Arg Ala
        595              600              605

Gly Val Thr Ala His Thr Gln Val Leu Ala Glu Glu Arg Thr Glu Arg
    610              615              620

Thr Ala Arg Gly Leu Leu Leu Arg Arg Leu Arg Arg Arg Asp Ser Gly
625              630              635              640

Val Tyr Leu Cys Ala Ala Val Glu Gln Gly Arg Thr Gln Pro Leu Arg
            645              650              655

Arg Leu Ser Leu His Val Leu Ser Ala Thr Gln Ala Glu Arg Leu Ala
        660              665              670

Arg Ala Glu Glu Ala Ala Pro Ala Ala Pro Pro Gly Pro Lys Leu Trp
        675              680              685

Tyr Arg Asp Phe Leu Gln Leu Val Glu Pro Gly Gly Gly Gly Ser Ala
    690              695              700

Asn Ser Leu Arg Met Cys Arg Pro Gln Pro Ala Leu Gln Ser Leu Pro
705              710              715              720

Leu Glu Ser Arg Arg Lys Gly Arg Asn Arg Arg Thr His Ala Pro Glu
            725              730              735

Pro Arg Ala Glu Arg Gly Pro Arg Ser Ala Thr His Trp
            740              745
```

<210> SEQ ID NO 2
<211> LENGTH: 13
<212> TYPE: PRT
<213> ORGANISM: Homo sapiens

<400> SEQUENCE: 2

```
Thr Cys Cys Tyr Gln Ala Leu Leu Val Asp Glu Glu Arg
1            5                10
```